(12) United States Patent
Ren et al.

(10) Patent No.: US 11,998,567 B2
(45) Date of Patent: Jun. 4, 2024

(54) ENGINEERED CHIMERIC GUIDE RNA AND USES THEREOF

(71) Applicant: NANJING BIOHENG BIOTECH CO., LTD., Nanjing (CN)

(72) Inventors: Jiangtao Ren, Nanjing (CN); Xuhua Zhang, Nanjing (CN)

(73) Assignee: NANJING BIOHENG BIOTECH CO., LTD., Nanjing (CN)

( * ) Notice: Subject to any disclaimer, the term of this patent is extended or adjusted under 35 U.S.C. 154(b) by 968 days.

(21) Appl. No.: 16/990,372

(22) Filed: Aug. 11, 2020

(65) Prior Publication Data

US 2020/0360439 A1 Nov. 19, 2020

Related U.S. Application Data

(63) Continuation of application No. PCT/CN2018/078697, filed on Mar. 12, 2018.

(51) Int. Cl.
| | |
|---|---|
| *A61K 35/17* | (2015.01) |
| *C12N 9/22* | (2006.01) |
| *C12N 15/10* | (2006.01) |
| *C12N 15/113* | (2010.01) |
| *C12N 15/63* | (2006.01) |

(52) U.S. Cl.
CPC ............... *A61K 35/17* (2013.01); *C12N 9/22* (2013.01); *C12N 15/102* (2013.01); *C12N 15/113* (2013.01); *C12N 15/63* (2013.01); *C12N 2310/20* (2017.05)

(58) Field of Classification Search
None
See application file for complete search history.

(56) References Cited

FOREIGN PATENT DOCUMENTS

| CN | 106244591 A | 12/2016 |
|---|---|---|
| CN | 107488649 A | 12/2017 |
| WO | 2016160721 A1 | 10/2016 |
| WO | 2017099494 A1 | 6/2017 |
| WO | 2017152015 A1 | 9/2017 |

OTHER PUBLICATIONS

Zhang, et al. (2018) "Genetic editing and interrogation with Cpf1 and caged truncated pre-tRNA-like crRNA in mammalian cells", Cell Discovery, 4:36, 10 pages. (Year: 2018).*
Xu, R.F. et al. "Generation of targeted mutant rice using a CRISPR-Cpf1 system," Plant Biotechnology Journal, vol. 15, Dec. 31, 2017.
Tang, X. et al. "A CRISPR-Cpf1 system for efficient genome editing and transcriptional repression in plants," Nature Plants, vol. 3, Feb. 17, 2017.

* cited by examiner

*Primary Examiner* — Robert M Kelly
(74) *Attorney, Agent, or Firm* — SZDC Law PC

(57) ABSTRACT

The present invention relates to engineered chimeric guide RNAs and their uses in systems and methods for gene expression perturbation in eukaryotic cells. Furthermore, the invention also relates to methods for generating a modified T cell using the engineered chimeric guide RNAs of the present application, and to the obtained modified T cell. Also included are methods and pharmaceutical compositions comprising the modified T cell for adoptive therapy and treating a condition, such as cancer, infections or autoimmune diseases.

4 Claims, 12 Drawing Sheets

Specification includes a Sequence Listing.

SEQUENCE LISTING

<160> NUMBER OF SEQ ID NOS: 61

<210> SEQ ID NO 1
<211> LENGTH: 50
<212> TYPE: DNA
<213> ORGANISM: Artificial sequence
<220> FEATURE:
<223> OTHER INFORMATION: DNMT1-crRNA

<400> SEQUENCE: 1
gaatttctac taagtgtaga tctgatggtc catgtctgtt actctttttt                50

<210> SEQ ID NO 2
<211> LENGTH: 50
<212> TYPE: DNA
<213> ORGANISM: Artificial sequence
<220> FEATURE:
<223> OTHER INFORMATION: VEGFa-crRNA

<400> SEQUENCE: 2

```
gaatttctac taagtgtaga tctaggaata ttgaaggggg caggttttt              50

<210> SEQ ID NO 3
<211> LENGTH: 50
<212> TYPE: DNA
<213> ORGANISM: Artificial sequence
<220> FEATURE:
<223> OTHER INFORMATION: GRIN2b-crRNA

<400> SEQUENCE: 3
gaatttctac taagtgtaga tgtgctcaat gaaaggagat aaggttttt              50

<210> SEQ ID NO 4
<211> LENGTH: 76
<212> TYPE: DNA
<213> ORGANISM: Artificial sequence
<220> FEATURE:
<223> OTHER INFORMATION: DNMT1-caRNA

<400> SEQUENCE: 4
gaatttctac taagtgtaga tctgatggtc catgtctgtt actcaatttc tactaagtgt  60 agatttttt aaaaaa                                                   76

<210> SEQ ID NO 5
<211> LENGTH: 76
<212> TYPE: DNA
<213> ORGANISM: Artificial sequence
<220> FEATURE:
<223> OTHER INFORMATION: VEGFa-caRNA

<400> SEQUENCE: 5
gaatttctac taagtgtaga tctaggaata ttgaaggggg caggaatttc tactaagtgt  60 agatttttt aaaaaa                                                   76

<210> SEQ ID NO 6
<211> LENGTH: 76
<212> TYPE: DNA
<213> ORGANISM: Artificial sequence
<220> FEATURE:
<223> OTHER INFORMATION: GRIN2b-caRNA

<400> SEQUENCE: 6
gaatttctac taagtgtaga tgtgctcaat gaaaggagat aaggaatttc tactaagtgt  60 agatttttt aaaaaa                                                   76

<210> SEQ ID NO 7
<211> LENGTH: 118
<212> TYPE: DNA
<213> ORGANISM: Artificial sequence
<220> FEATURE:
<223> OTHER INFORMATION: DNMT1-csRNA

<400> SEQUENCE: 7
gccagtggtc tagtggtaga atagtaccct gccacggtac agacccgggt tcgattcccg  60
gctggaaata atttctacta agtgtagatc tgatggtcca tgtctgttac tcttttt    118

<210> SEQ ID NO 8
<211> LENGTH: 118
<212> TYPE: DNA
<213> ORGANISM: Artificial sequence
<220> FEATURE:
<223> OTHER INFORMATION: VEGFa-csRNA

<400> SEQUENCE: 8
```

```
gccagtggtc tagtggtaga atagtaccct gccacggtac agacccgggt tcgattcccg    60
gctggaaata atttctacta agtgtagatc taggaatatt gaaggggca ggttttttt    118

<210> SEQ ID NO 9
<211> LENGTH: 124
<212> TYPE: DNA
<213> ORGANISM: Artificial sequence
<220> FEATURE:
<223> OTHER INFORMATION: GRIN2b-csRNA

<400> SEQUENCE: 9
gccagtggtc tagtggtaga atagtaccct gccacggtac agacccgggt tcgattcccg    60
gctggaaata atttctacta agtgtagatg tgctcaatga aggagataa ggttttttaa   120 aaaa                                                                124

<210> SEQ ID NO 10
<211> LENGTH: 144
<212> TYPE: DNA
<213> ORGANISM: Artificial sequence
<220> FEATURE:
<223> OTHER INFORMATION: DNMT1-catRNA

<400> SEQUENCE: 10
gccagtggtc tagtggtaga atagtaccct gccacggtac agacccgggt tcgattcccg    60
gctggaaata atttctacta agtgtagatc tgatggtcca tgtctgttac tcaatttcta   120
ctaagtgtag attttttta aaaa                                           144

<210> SEQ ID NO 11
<211> LENGTH: 144
<212> TYPE: DNA
<213> ORGANISM: Artificial sequence
<220> FEATURE:
<223> OTHER INFORMATION: VEGFa-catRNA

<400> SEQUENCE: 11
gccagtggtc tagtggtaga atagtaccct gccacggtac agacccgggt tcgattcccg    60
gctggaaata atttctacta agtgtagatc taggaatatt gaaggggca ggaatttcta   120 ctaagtgtag attttttta aaaa                                           144

<210> SEQ ID NO 12
<211> LENGTH: 144
<212> TYPE: DNA
<213> ORGANISM: Artificial sequence
<220> FEATURE:
<223> OTHER INFORMATION: GRIN2b-catRNA

<400> SEQUENCE: 12
gccagtggtc tagtggtaga atagtaccct gccacggtac agacccgggt tcgattcccg    60
gctggaaata atttctacta agtgtagatg tgctcaatga aggagataa ggaatttcta   120 ctaagtgtag attttttta aaaa                                           144

<210> SEQ ID NO 13
<211> LENGTH: 23
<212> TYPE: DNA
<213> ORGANISM: Artificial sequence
<220> FEATURE:
<223> OTHER INFORMATION: DNMT1-1

<400> SEQUENCE: 13
```

```
tcagcaccat tgttaaaga cac                                              23

<210> SEQ ID NO 14
<211> LENGTH: 23
<212> TYPE: DNA
<213> ORGANISM: Artificial sequence
<220> FEATURE:
<223> OTHER INFORMATION: DNMT1-2

<400> SEQUENCE: 14
cgcgcgaaaa gccggggcgc ctg                                             23

<210> SEQ ID NO 15
<211> LENGTH: 23
<212> TYPE: DNA
<213> ORGANISM: Artificial sequence
<220> FEATURE:
<223> OTHER INFORMATION: DNMT1-3

<400> SEQUENCE: 15
tgagagccct tgagtaaagt cct                                             23

<210> SEQ ID NO 16
<211> LENGTH: 23
<212> TYPE: DNA
<213> ORGANISM: Artificial sequence
<220> FEATURE:
<223> OTHER INFORMATION: VEGFa-1

<400> SEQUENCE: 16
tgacctccca aacagctaca tat                                             23

<210> SEQ ID NO 17
<211> LENGTH: 23
<212> TYPE: DNA
<213> ORGANISM: Artificial sequence
<220> FEATURE:
<223> OTHER INFORMATION: VEGFa-2

<400> SEQUENCE: 17
ctgctccctc ctcgccaatg ccc                                             23

<210> SEQ ID NO 18
<211> LENGTH: 23
<212> TYPE: DNA
<213> ORGANISM: Artificial sequence
<220> FEATURE:
<223> OTHER INFORMATION: VEGFa-3

<400> SEQUENCE: 18
tccccaaatc actgtggatt ttg                                             23

<210> SEQ ID NO 19
<211> LENGTH: 24
<212> TYPE: DNA
<213> ORGANISM: Artificial sequence
<220> FEATURE:
<223> OTHER INFORMATION: DNMT1-24bp

<400> SEQUENCE: 19
ctgatggtcc atgtctgtta ctcg                                            24

<210> SEQ ID NO 20
<211> LENGTH: 20
<212> TYPE: DNA
<213> ORGANISM: Artificial sequence
```

```
<220> FEATURE:
<223> OTHER INFORMATION: DNMT1-20bp

<400> SEQUENCE: 20
ctgatggtcc atgtctgtta                                                    20

<210> SEQ ID NO 21
<211> LENGTH: 18
<212> TYPE: DNA
<213> ORGANISM: Artificial sequence
<220> FEATURE:
<223> OTHER INFORMATION: DNMT1-18bp

<400> SEQUENCE: 21
ctgatggtcc atgtctgt                                                      18

<210> SEQ ID NO 22
<211> LENGTH: 17
<212> TYPE: DNA
<213> ORGANISM: Artificial sequence
<220> FEATURE:
<223> OTHER INFORMATION: DNMT1-17bp

<400> SEQUENCE: 22
ctgatggtcc atgtctg                                                       17

<210> SEQ ID NO 23
<211> LENGTH: 16
<212> TYPE: DNA
<213> ORGANISM: Artificial sequence
<220> FEATURE:
<223> OTHER INFORMATION: DNMT1-16bp

<400> SEQUENCE: 23
ctgatggtcc atgtct                                                        16

<210> SEQ ID NO 24
<211> LENGTH: 15
<212> TYPE: DNA
<213> ORGANISM: Artificial sequence
<220> FEATURE:
<223> OTHER INFORMATION: DNMT1-15bp

<400> SEQUENCE: 24
ctgatggtcc atgtc                                                         15

<210> SEQ ID NO 25
<211> LENGTH: 14
<212> TYPE: DNA
<213> ORGANISM: Artificial sequence
<220> FEATURE:
<223> OTHER INFORMATION: DNMT1-14bp

<400> SEQUENCE: 25
ctgatggtcc atgt                                                          14

<210> SEQ ID NO 26
<211> LENGTH: 24
<212> TYPE: DNA
<213> ORGANISM: Artificial sequence
<220> FEATURE:
<223> OTHER INFORMATION: VEGFa-24bp

<400> SEQUENCE: 26
ctaggaatat tgaaggggggc aggg                                              24
```

<210> SEQ ID NO 27
<211> LENGTH: 20
<212> TYPE: DNA
<213> ORGANISM: Artificial sequence
<220> FEATURE:
<223> OTHER INFORMATION: VEGFa-20bp

<400> SEQUENCE: 27
ctaggaatat tgaaggggc                                          20

<210> SEQ ID NO 28
<211> LENGTH: 18
<212> TYPE: DNA
<213> ORGANISM: Artificial sequence
<220> FEATURE:
<223> OTHER INFORMATION: VEGFa-18bp

<400> SEQUENCE: 28
ctaggaatat tgaagggg                                           18

<210> SEQ ID NO 29
<211> LENGTH: 17
<212> TYPE: DNA
<213> ORGANISM: Artificial sequence
<220> FEATURE:
<223> OTHER INFORMATION: VEGFa-17bp

<400> SEQUENCE: 29
ctaggaatat tgaaggg                                            17

<210> SEQ ID NO 30
<211> LENGTH: 16
<212> TYPE: DNA
<213> ORGANISM: Artificial sequence
<220> FEATURE:
<223> OTHER INFORMATION: VEGFa-16bp

<400> SEQUENCE: 30
ctaggaatat tgaagg                                             16

<210> SEQ ID NO 31
<211> LENGTH: 15
<212> TYPE: DNA
<213> ORGANISM: Artificial sequence
<220> FEATURE:
<223> OTHER INFORMATION: VEGFa-15bp

<400> SEQUENCE: 31
ctaggaatat tgaag                                              15

<210> SEQ ID NO 32
<211> LENGTH: 14
<212> TYPE: DNA
<213> ORGANISM: Artificial sequence
<220> FEATURE:
<223> OTHER INFORMATION: VEGFa-14bp

<400> SEQUENCE: 32
ctaggaatat tgaa                                               14

<210> SEQ ID NO 33
<211> LENGTH: 23
<212> TYPE: DNA
<213> ORGANISM: Artificial sequence
<220> FEATURE:
<223> OTHER INFORMATION: TCRalpha-1

-continued

```
<400> SEQUENCE: 33
attctcaaac aaatgtgtca caa                                              23

<210> SEQ ID NO 34
<211> LENGTH: 23
<212> TYPE: DNA
<213> ORGANISM: Artificial sequence
<220> FEATURE:
<223> OTHER INFORMATION: TCRalpha-2

<400> SEQUENCE: 34
catgtgcaaa cgccttcaac aac                                              23

<210> SEQ ID NO 35
<211> LENGTH: 23
<212> TYPE: DNA
<213> ORGANISM: Artificial sequence
<220> FEATURE:
<223> OTHER INFORMATION: TCRalpha-3

<400> SEQUENCE: 35
cacatgcaaa gtcagatttg ttg                                              23

<210> SEQ ID NO 36
<211> LENGTH: 23
<212> TYPE: DNA
<213> ORGANISM: Artificial sequence
<220> FEATURE:
<223> OTHER INFORMATION: TCRalpha-4

<400> SEQUENCE: 36
ttgctccagg ccacagcact gtt                                              23

<210> SEQ ID NO 37
<211> LENGTH: 23
<212> TYPE: DNA
<213> ORGANISM: Artificial sequence
<220> FEATURE:
<223> OTHER INFORMATION: TCRalpha-5

<400> SEQUENCE: 37
tctgtgatat acacatcaga atc                                              23

<210> SEQ ID NO 38
<211> LENGTH: 23
<212> TYPE: DNA
<213> ORGANISM: Artificial sequence
<220> FEATURE:
<223> OTHER INFORMATION: TCRalpha-6

<400> SEQUENCE: 38
tgacacattt gtttgagaat caa                                              23

<210> SEQ ID NO 39
<211> LENGTH: 23
<212> TYPE: DNA
<213> ORGANISM: Artificial sequence
<220> FEATURE:
<223> OTHER INFORMATION: TCRalpha-7

<400> SEQUENCE: 39
tttgagaatc aaaatcggtg aat                                              23

<210> SEQ ID NO 40
```

```
<211> LENGTH: 23
<212> TYPE: DNA
<213> ORGANISM: Artificial sequence
<220> FEATURE:
<223> OTHER INFORMATION: TCRalpha-8

<400> SEQUENCE: 40
agaatcaaaa tcggtgaata ggc                                              23

<210> SEQ ID NO 41
<211> LENGTH: 23
<212> TYPE: DNA
<213> ORGANISM: Artificial sequence
<220> FEATURE:
<223> OTHER INFORMATION: TCRalpha-9

<400> SEQUENCE: 41
gagtctctca gctggtacac ggc                                              23

<210> SEQ ID NO 42
<211> LENGTH: 23
<212> TYPE: DNA
<213> ORGANISM: Artificial sequence
<220> FEATURE:
<223> OTHER INFORMATION: TCRbeta-1

<400> SEQUENCE: 42
agccatcaga agcagagatc tcc                                              23

<210> SEQ ID NO 43
<211> LENGTH: 24
<212> TYPE: DNA
<213> ORGANISM: Artificial sequence
<220> FEATURE:
<223> OTHER INFORMATION: TCRbeta-2

<400> SEQUENCE: 43
cctcggtgtc ctaccagcaa gggg                                             24

<210> SEQ ID NO 44
<211> LENGTH: 24
<212> TYPE: DNA
<213> ORGANISM: Artificial sequence
<220> FEATURE:
<223> OTHER INFORMATION: TCRbeta-3

<400> SEQUENCE: 44
gccctatcct gggtccactc gtca                                             24

<210> SEQ ID NO 45
<211> LENGTH: 24
<212> TYPE: DNA
<213> ORGANISM: Artificial sequence
<220> FEATURE:
<223> OTHER INFORMATION: TCRbeta-4

<400> SEQUENCE: 45
ggtgtgggag atctctgctt ctga                                             24

<210> SEQ ID NO 46
<211> LENGTH: 23
<212> TYPE: DNA
<213> ORGANISM: Artificial sequence
<220> FEATURE:
<223> OTHER INFORMATION: CD52-1

<400> SEQUENCE: 46
```
tatctgtacc ataaccagga ggc                                    23

<210> SEQ ID NO 47
<211> LENGTH: 23
<212> TYPE: DNA
<213> ORGANISM: Artificial sequence
<220> FEATURE:
<223> OTHER INFORMATION: CD52-2

<400> SEQUENCE: 47
tcctgagagt ccagtttgta tct                                    23

<210> SEQ ID NO 48
<211> LENGTH: 23
<212> TYPE: DNA
<213> ORGANISM: Artificial sequence
<220> FEATURE:
<223> OTHER INFORMATION: CD52-3

<400> SEQUENCE: 48
gctggtgtcg ttttgtcctg aga                                    23

<210> SEQ ID NO 49
<211> LENGTH: 23
<212> TYPE: DNA
<213> ORGANISM: Artificial sequence
<220> FEATURE:
<223> OTHER INFORMATION: CD52-4

<400> SEQUENCE: 49
cttttcttcg tggccaatgc cat                                    23

<210> SEQ ID NO 50
<211> LENGTH: 23
<212> TYPE: DNA
<213> ORGANISM: Artificial sequence
<220> FEATURE:
<223> OTHER INFORMATION: CD52-5

<400> SEQUENCE: 50
ttcgtggcca atgccataat cca                                    23

<210> SEQ ID NO 51
<211> LENGTH: 23
<212> TYPE: DNA
<213> ORGANISM: Artificial sequence
<220> FEATURE:
<223> OTHER INFORMATION: B2m-1

<400> SEQUENCE: 51
atccatccga cattgaagtt gac                                    23

<210> SEQ ID NO 52
<211> LENGTH: 23
<212> TYPE: DNA
<213> ORGANISM: Artificial sequence
<220> FEATURE:
<223> OTHER INFORMATION: B2m-2

<400> SEQUENCE: 52
gctgtgctcg cgctactctc tct                                    23

<210> SEQ ID NO 53
<211> LENGTH: 24
<212> TYPE: DNA

<210> SEQ ID NO 53
<211> LENGTH: 24
<212> TYPE: DNA
<213> ORGANISM: Artificial sequence
<220> FEATURE:
<223> OTHER INFORMATION: PD-1

<400> SEQUENCE: 53
accttccgct cacctccgcc tgag                                    24

<210> SEQ ID NO 54
<211> LENGTH: 23
<212> TYPE: DNA
<213> ORGANISM: Artificial sequence
<220> FEATURE:
<223> OTHER INFORMATION: PD-2

<400> SEQUENCE: 54
tgcccttcca gagagaaggg cag                                     23

<210> SEQ ID NO 55
<211> LENGTH: 23
<212> TYPE: DNA
<213> ORGANISM: Artificial sequence
<220> FEATURE:
<223> OTHER INFORMATION: PD-3

<400> SEQUENCE: 55
tctgcaggga caataggagc cag                                     23

<210> SEQ ID NO 56
<211> LENGTH: 23
<212> TYPE: DNA
<213> ORGANISM: Artificial sequence
<220> FEATURE:
<223> OTHER INFORMATION: PD-4

<400> SEQUENCE: 56
tcctcaaaga aggaggaccc ctc                                     23

<210> SEQ ID NO 57
<211> LENGTH: 23
<212> TYPE: DNA
<213> ORGANISM: Artificial sequence
<220> FEATURE:
<223> OTHER INFORMATION: PD-5

<400> SEQUENCE: 57
cagtggcgag agaagacccc gga                                     23

<210> SEQ ID NO 58
<211> LENGTH: 23
<212> TYPE: DNA
<213> ORGANISM: Artificial sequence
<220> FEATURE:
<223> OTHER INFORMATION: PD-6

<400> SEQUENCE: 58
ctagcggaat gggcacctca tcc                                     23

<210> SEQ ID NO 59
<211> LENGTH: 23
<212> TYPE: DNA
<213> ORGANISM: Artificial sequence
<220> FEATURE:
<223> OTHER INFORMATION: PD-7

<400> SEQUENCE: 59
ctcaggagaa gcaggcaggg tgc                                     23

```
<210> SEQ ID NO 60
<211> LENGTH: 23
<212> TYPE: DNA
<213> ORGANISM: Artificial sequence
<220> FEATURE:
<223> OTHER INFORMATION: PD-8

<400> SEQUENCE: 60
caacacatcg gagagcttcg tgc                                           23

<210> SEQ ID NO 61
<211> LENGTH: 23
<212> TYPE: DNA
<213> ORGANISM: Artificial sequence
<220> FEATURE:
<223> OTHER INFORMATION: PD-9

<400> SEQUENCE: 61
atctgcgcct tggggggccag gga                                          23
```

ENGINEERED CHIMERIC GUIDE RNA AND USES THEREOF

This application is a Continuation Application of PCT/CN2018/078697, filed on Mar. 12, 2018, which is incorporated by reference for all purposes as if fully set forth herein.

FIELD OF THE INVENTION

The present invention relates to engineered chimeric guide RNAs and their uses in systems and methods for altering gene expression in eukaryotic cells for the purpose of gene correction or disease treatment. Furthermore, the invention also relates to methods for generating a modified T cell using the engineered chimeric guide RNAs of the present application, and to the obtained modified T cell, particularly non-alloreactive T-cells for immunotherapy. Also included are methods and pharmaceutical compositions comprising the modified T cell for adoptive therapy and treating a condition, such as cancer, infections or autoimmune diseases.

BACKGROUND OF THE INVENTION

Over a century, immunology has been extensively employed for the treatment of malignant tumors, such as monoclonal antibody (mAb), bispecific antibody, tumor vaccine, immune checkpoint blockade, Dendritic cells (DC), cytokine-induced killer (CIK), tumor-infiltrating lymphocytes (TIL), and most recently chimeric antigen receptor T cells (CART). Among these approaches, adoptive immunotherapy, which involves the transfer of autologous antigen-specific T cells generated ex vivo, is a promising and fast evolving strategy to treat viral infections and cancers. The T cells utilized for adoptive immunotherapy can be produced either by expansion of antigen-specific T cells or re-direction of T cells through genetic reprogramming.

Transfer of viral antigen specific T cells is a well-established procedure used for the treatment of transplant associated viral infections and rare viral-related malignancies. Similarly, isolation and transfer of tumor specific T cells has been shown to be successful in treating melanoma. Moreover, specificities in T cells have been successfully re-directed through the genetic transfer of transgenic T cell receptors (TCR) or chimeric antigen receptors (CARs). The CART-based immunotherapy has achieved significant progress in malignant hematological diseases, including various leukemia and lymphomas and may eventually be used to treat solid cancers. CARs comprise an extracellular single-chain variable variant (ScFv) specific to an antigen of tumor cells, a co-stimulatory domain (CD28, 41BB, OX40, CD40 and the like) and an intracellular signaling domain that drives T cell activation and the killing of tumor cells. To date, the best CART cell therapy involves targeting CD19, an antigen expressed by B cells and B cell malignancies. As a breakthrough immunocellular therapy for children and young adults who desperately need new options, Kymriah (CTLo19) was approved by the US Food and Drug Administration (FDA) in August 2017, followed by a second personalized CART cell therapy-Yescarta for the treatment of Diffused large B cell lymphoma (DLBCL) in November 2017. The most recent clinical studies with a CART cell targeting B cell maturation antigen (BCMA) carried by Blue bird Bio and Legend both yields very high response rate. Several other CART adoptive immunotherapies against solid tumor antigens, such as Her2/neu, Mesothelin, c-Met, GD2, interleukin-13 receptor alpha 2 (IL13Ra2), CEA, and EGFR, are currently under evaluation in different phases of clinical trials.

Most of the current CART therapies are based on the manufacture of autologous T cells and might therefore be hampered by the poor quality and quantity of T cells and by the time and expense of manufacturing autologous T cell products. CART cell therapy could substantially benefit from allogeneic universal donor T cells, as "off-the-shelf" cells could greatly increase the number of patients who could be treated by a single CART cell product, as well as reduce the timeline for CART cell manufacture. However, endogenous TCR on allogeneic T cells may recognize the alloantigens of the recipient, leading to graft-versus-host disease (GVHD). Furthermore, the expression of HLA on the surface of allogeneic T cells renders rapid rejection by the host immune system. In this context, ZFNs, TALENs and CRISPRs have been used to knock out endogenous T cell receptor genes in T cells, which could prevent unwanted graft-versus-host reactivity. Genome-editing strategies could also be used to prevent or delay the rejection of CART cells by the recipient's immune system by eliminating or decreasing the expression of histocompatibility antigens on the donor T cells. Other methods including knocking out antibody or chemotherapy sensitive genes (such as CD52 or dCK) have been developed for propagation of drug-resistant CART cell populations.

Although ZFNs and TALENs have been adopted to ablate endogenous TCR and related genes, the overall gene knock-out efficiency is far from desirable. Besides, the design of ZFNs and TALENs is complicated and time-consuming: the function of ZFNs and TALENs require a pair of effector proteins which make the multiplex genome editing difficult to achieve; the chromosome translocations associated with TALEN gene editing in universal CART19 (UCART19) cells used by Cellectis in their clinical study is a serious problem which may results in unwanted oncogenesis potential; last but not least, the purification cost resulting from the low gene editing efficiency makes TALEN not desirable for UCART cell production. Given these difficulties, their potential for large-scale genomic manipulation is limited.

Recently, a new genome-engineering tool has been developed based on the components of the type II prokaryotic CRISPR (Clustered Regularly Interspaced Short palindromic Repeats). The CRISPR technology originates from type II CRISPR systems, which provide bacteria with adaptive immunity to viruses, plasmids, and other foreign nucleic acids. Type II CRISPR systems incorporate sequences from invading DNA between CRISPR repeat sequences that are encoded as arrays within the bacterial host genome. Transcripts from the CRISPR repeat arrays are processed into CRISPR RNAs (crRNAs), each containing a variable sequence transcribed from the invading DNA, which is known as the "protospacer" sequence, and part of the CRISPR repeat. Each crRNA hybridizes with a second RNA, which is known as the transactivating CRISPR RNA (tracrRNA), and these two RNAs form a complex with the Cas9 DNA endonuclease. The protospacer-encoded portion of the crRNA guides Cas9 to complementary target DNA sequences and cleaves the DNA if they are adjacent to short sequences known as protospacer adjacent motifs (PAMs). The type II CRISPR system from *Streptococcus pyogenes* has been adapted for inducing sequence-specific double-strand breaks (DSBs) and targeted genome editing. In 2012, Jinek et al. first demonstrated that the Cas9 protein from *Streptococcus pyogenes* (SpCas9) can bind with a tracrRNA-crRNA RNA complex to induce DSBs in vitro at a target DNA sequence by Watson-Crick base pairing between the crRNA and target DNA. This study also showed that directing Cas9 to bind and cleave a specific DNA sequence did not require an RNA complex. The process can be simply achieved by using a designed, single guide RNA (sgRNA). In 2013, two groups from MIT and Harvard demonstrated the feasibility of genome editing of human cells using the CRISPR/Cas9 system. These discoveries paved the way and opened the era for the use of CRISPR/Cas9 in genome engineering, including gene editing and gene expression regulation, epigenetic modification, and genome imaging.

In previous studies, several groups reported the use of the CRISPR/Cas9 system to disrupt TCR, B2m, PD1, CTLA4, CCR5, CXCR4, Lag3 and the like in T cells with efficiency ranging from 7% to over 90% using different protocols. CRISPR may greatly advance CART cell therapy in certain ways. Indeed, a clinical trial has recently been approved by the US National Institutes of Health (NIH) Recombinant DNA Advisory Committee (RAC) that will be conducted at the University of Pennsylvania. In this clinical trial, PD1 and the endogenous TCR will be knocked out by CRISPR/Cas9 in NY-ESO-1 TCR transduced T cells. The first clinical trial of CRISPR/Cas9 has been initiated. The trial uses CRISPR/Cas9 to knock out PD1 in T cells of patients with lung cancer; however, CAR or TCR will not be introduced into T cells in this trial. Scientists are seeking to introduce CAR via HDR to eliminate the need of randomly integration of viral delivery systems and to control where CAR integrates. A recent study showed that targeting a CAR to the TRAC locus greatly enhanced the antitumor activity by reducing tonic activation.

In addition to the type II CRISPR, a new type V CRISPR has been discovered in recent years. To date, the experimentally tested type V CRISPR systems include the use of the following effector proteins which have been redesignated as Cas12a-e: Cas12a (also known as Cpf1; subtype V-A), Cas12b (also known as C2c1; subtype V-B), Cas12c (also known as C2c3; subtype V-C), Cas12d (also known as CasY; subtype V-D) and Cas12e (also known as CasX; subtype V-E), all of which are evolutionarily distinct from Cas9.

Similarly to Cas9, Cpf1 proteins contain a conserved RuvC nuclease domain that is known to hydrolyse single-stranded DNA (ssDNA). However, Cpf1 has features distinct from those of Cas9. It is a single RNA-guided endonuclease that recognizes thymidine-rich protospacer adjacent motifs (PAMs) and produces staggered cuts distal to the PAM site. This type V CRISPR/Cpf1 system has demonstrated robust genome editing activity in eukayotic cells as well as in animals, plants and bacteria. Interestingly, Cpf1 is a dual nuclease that not only cleaves target DNA but also processes its own CRISPR RNA (crRNA), and this processing of its own crRNA is independently carried out by a second catalytic domain of Cpf1. In addition, the maturation of crRNA by Cpf1 does not require assistance from trans-activating crRNA (tracrRNA). Harboring these advantages, the Cpf1 system was recently adopted for multiplex gene editing in eukaryotic cells, in particular in plant cells, wherein up to four genes were simultaneously edited by Cpf1 using a single crRNA array spaced by mature direct repeats.

Besides the differential choice for PAM sequences and multiplex gene editing with a single crRNA transcript, compared with the high off-target potential of Cas9, genome-wide deep sequencing revealed very precise gene disruption by Cpf1, all of these features making Cpf1 an ideal gene modification competitor to Cas9.

Although Cpf1 mediates efficient gene editing in eukaryotic cells, its overall activity is not as robust as that of Cas9. Its use in primary cells, in particular in TCells, is significantly limited by the fact that:

the low targeting efficiency of conventional crRNA and Cpf1 makes it difficult for its application in T cells;
the quality, viability of T cells could be adversely affected by the introduction of DNA in their cytoplasm, as high rate of apoptosis is observed when transforming cells with DNA vectors;
efficient gene editing with the Cpf1 system requires stable expression of Cpf1 protein in the cells. However, prolonged expression of Cpf1 in living cells can lead to chromosomal defects and T cell apoptosis due to unknown reason.

The present application aims to provide solutions to these limitations in order to efficiently perturbate gene expression in T cells. Surprisingly, the inventors developed an engineered chimeric crRNAs, including caRNAs, csRNAs and catRNAs, which provide RNase-resistant activity and higher efficiency of gene editing in eukaryotic cells, especially in T cells, compared to conventional crRNAs, thus enabling the establishment of a simple approach for selective gene perturbation and standard and affordable adoptive immunotherapy strategies.

SUMMARY OF THE INVENTION

In the first aspect, the present invention relates to an engineered chimeric guide RNA comprising: (1) at least one crRNA sequences, and (2) at least one additional direct repeat sequences or small RNA species or both, wherein the crRNA sequence is capable of hybridizing with a target locus of interest, and the additional direct repeat sequence and/or the small RNA species confers increased stability of the chimeric guide RNA. In one specific embodiment, the engineered chimeric guide RNA is a caRNA comprising at least one crRNA sequence and at least one direct repeat sequences. In one specific embodiment, the engineered chimeric guide RNA is a csRNA comprising at least one crRNA sequence and at least one small RNA species. In a further embodiment, the engineered chimeric guide RNA is a catRNA comprising at least one crNRA sequence and at least one direct repeat sequences and small RNA species.

In one embodiment, the at least one crRNA sequences are same or different. In one embodiment, the at least one additional direct repeat sequences are same or different. In one embodiment, the at least one small RNA species are same or different.

In one embodiment, the small RNA species are selected from the group consisting of transfer RNA (tRNA), microRNA (miRNA), Piwi-interacting RNA (piRNA), small interfering RNA (siRNA), small nucleolar RNA (snoRNA), tRNA-derived small RNA (tsRNA), small rDNA-derived RNA (srRNA), long non-coding RNA (lncRNA), small nuclear RNA (U-RNA), short-hairpin RNA (shRNA), pre-tRNA as well as messenger RNA (mRNA). Preferably, the small RNA species is tRNA or pre-tRNA.

In one embodiment, said small RNA species is in a truncated form. Preferably, the small RNA species is a truncated form of pre-tRNA.

In a further embodiment, the engineered chimeric guide RNA further comprises untranslated region (UTR), poly-A and/or 5' methylguanosine cap.

In one specific embodiment, the crRNA contained in the engineered chimeric guide RNA comprises at least one spacer sequence, which spacer sequence has a length from 10 to 30 bp, preferably from 16 to 24 bp.

In one embodiment, the engineered chimeric guide RNAs target one or more loci of interest, wherein said loci of interest are located in the same or different DNA sequences.

In one embodiment, the engineered chimeric guide RNAs present in the form of a pool or an array.

In the second aspect, the present invention relates to a CRISPR/Cpf1 system comprising:
 (a) one or more engineered chimeric guide RNAs according to the present application, or one or more polynucleotide sequences encoding the engineered chimeric guide RNAs according to the present application; and
 (b) a Cpf1 protein or a functional variant thereof, or one or more polynucleotide sequences encoding the Cpf1 protein or a functional variant thereof.

In one embodiment, the components (a) and (b) are polynucleotide sequences located on the same vector. Alternatively, the components (a) and (b) are polynucleotide sequences located on different vectors.

In one embodiment, the system further comprises $Mg^{2+}$, preferably at a concentration from about 1 mM to about 15 mM.

In one embodiment, the Cpf1 protein or a functional variant of is derived from a bacterial species selected from *Francisella tularensis* 1, *Francisella tularensis* subsp. *novicida*, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum*, *Eu-bacterium eligens*, *Moraxella bovoculi* 237, *Leptospira inadai*, Lachnospiraceae bacterium ND2006, *Porphyromonas crevioricanis* 3, *Prevotella disiens* and *Por-phyromonas macacae*. Preferably, the Cpf1 protein or a functional variant thereof is derived from *Prevotella albensis* (PaCpf1), Lachnospiraceae bacterium ND2006 (LbCpf1), *Francisella tularensis* subsp. *novicida* (FnCpf1), or *Acidaminococcus* sp. BV3L6 (AsCpf1).

The engineered chimeric guide RNA according to the present application hybridizes to a target sequence, wherein said target sequence is 3' of a Protospacer Adjacent Motif (PAM). Preferably, the PAM comprises a 5' T-rich motif.

Specifically, when the PAM sequence is TTN and N is A/C/G or T, the Cpf1 protein is FnCpf1; when the PAM sequence is TTTN and N is A/C or G, the Cpf1 protein is PaCpf1, LbCpf1 or AsCpf1.

In one embodiment, the Cpf1 protein or a functional variant thereof comprises one or more nuclear localization signals.

The present invention also encompasses a cell or cell line or progeny thereof comprising the above system according to the present invention.

In the third aspect, the present invention provides a method of modifying a target locus of interest, comprising delivering to said locus the CRISPR/Cpf1 system according to the present application. The components (a) and (b) of the CRISPR/Cpf1 system are delivered together or separately.

The present invention also provides a method of altering expression of at least one target gene, comprising introducing the CRISPR/Cpf1system according to the present application into a cell comprising said target gene. The components (a) and (b) of the system can be introduced together or separately.

In one embodiment, the target locus of interest is within a cell, for example a eukaryotic cell, such as an animal, human or plant cell. In another embodiment, the target locus is comprised in a DNA molecule in vitro.

In the fourth aspect, the present invention provides a method of preparing engineered T-cells for immunotherapy, comprising the steps of genetically modifying the T cells by introducing into the cells and/or expression in the T cells a system comprising at least:
 a Cpf1 protein or a functional variant thereof, or one or more polynucleotide sequences encoding the Cpf1 protein or a functional variant thereof; and
 one or more engineered chimeric guide RNAs according to the present application, or one or more polynucleotide sequences encoding the engineered chimeric guide RNAs according to the present application.

In one embodiment, the method of preparing engineered T-cells further comprises a step of (b) expanding the engineered T cells in vitro.

In one embodiment, the method of preparing engineered T-cells further comprises a step of (b) transducing chimeric antigen receptors (CARs) into the T cells. In particular, the step (b) is performed before, after or at the same time with the step (a) of genetically modifying the T cells.

In a specific embodiment, the T cells are derived from peripheral blood mononuclear cell (PBMC) or cord blood. Preferably, the T cells are derived from inflammatory T-lymphocytes, cytotoxic T-lymphocytes, regulatory T-lymphocytes or helper T-lymphocytes, in particularly CD4+T-lymphocytes and/or CD8+T-lymphocytes.

The present invention also provides the engineered T cells, in particular allogeneic T cells prepared according to the above method of the present invention.

In a further embodiment, the engineered T cells further comprise exogenous recombinant polynucleotides encoding CARs for specific cell recognition.

In particular, the engineered T cells according to the present invention are used as a pharmaceutical composition product, ideally as an "off the shelf" product, for treating or preventing cancer, infections or auto-immune disease.

DETAILED DESCRIPTION OF THE INVENTION

Definitions

The following definitions are provided to better define the present invention and to guide those of ordinary skill in the art in the practice of the present invention. Unless otherwise noted, terms are to be understood according to conventional usage by those of ordinary skill in the relevant art.

The term "CRISPR" refers to Clustered Regularly Interspaced Short Palindromic Repeats. CRISPR was initially described as segments of prokaryotic DNA containing short, repetitive base sequences. In a palindromic repeat, the sequence of nucleotides is the same in both directions. Each repetition is followed by short segments of spacer DNA from previous exposures to foreign DNA (e.g., a virus or plasmid). CRISPR loci typically consist of a clustered set of CRISPR-associated (Cas) genes and the signature CRISPR array-a series of repeat sequences (direct repeats) interspaced by variable sequences(spacers) corresponding to sequences within foreign genetic elements (protospacers). Whereas Cas genes are translated into proteins, most CRISPR arrays are first transcribed as a single RNA before subsequent processing into shorter CRISPR RNAs (crRNAs), which direct the nucleolytic activity of certain Cas enzymes to degrade target nucleic acids.

The term "CRISPR/Cas system" refers to a prokaryotic immune system that confers resistance to foreign genetic elements such as those present within plasmids and phages that provides a form of acquired immunity. Generally, CRISPR/Cas system comprises at least a Cas endonuclease and a guide RNA. the RNA harboring the spacer sequence helps Cas (CRISPR-associated) proteins recognize and cut exogenous DNA. Accordingly, when the Cas protein is Cpf1, the system is called CRISPR/Cpf1 system.

The term "Cas9" refers to one kind of Cas protein that found in *Streptococcus pyogenes*. The Cas9 endonuclease is a four-component system that includes two small RNA molecules named CRISPR RNA (crRNA) and trans-activating CRISPR RNA (tracrRNA).

The term "Cpf1" refers to an RNA-guided DNA endonuclease that belongs to a subtype V-A of class II CRISPR system obtained from *Prevotella* and *Francisella* 1. The Cpf1 endonuclease contains a conserved RuvC nuclease domain that is known to hydrolyse single-stranded DNA (ssDNA) and a second catalytic domain, which is responsible for the independent processing of its own crRNA. It has been reported that the maturation of crRNA by Cpf1 does not require assistance from tracrRNA.

The term "guide RNA" or "gRNA" generally refers to a RNA molecule, which directs the Cas endonuclease to the target locus and specifically hybridizes to the complementary sequence within the target locus, thereby causing double strand break in the target locus under the action of the endonuclease. gRNA include but not limited to crRNA, sgRNA and other chimeric guide RNAs such as caRNA, csRNA, catRNA according to the present invention.

Figure 1:
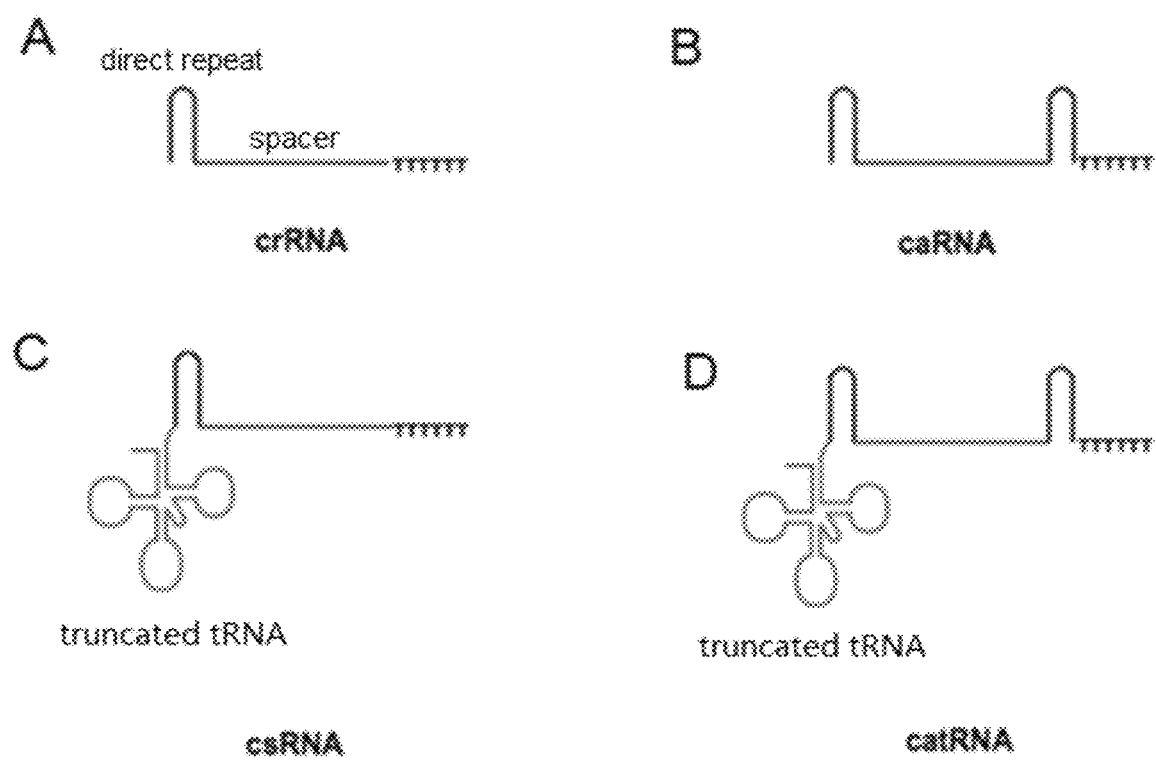
FIG. 1: An example of crRNA (A), caRNA (B), csRNA (C) and catRNA (D) structures.

In a typical CRISPR system, guide RNA is crRNA, which generally comprises a direct repeat and a spacer sequence (FIG. 1A). "Direct repeat" refers to repeat sequences interspaced by variable sequences (spacer) within CRISPR locus. "Spacer" refers to viral DNA inserted into a CRISPR locus created from invading viral or plasmid DNA (called "protospacers"). The wild-type Cas9 has a spacer sequence with a length of 20 bp, while the full-length spacer in crRNA of wild type Cpf1 is 24 bp. The crRNA will direct the Cas protein to the invading protospacer sequence on subsequent invasion. But Cas proteins will not cleave the protospacer sequence unless there is an adjacent PAM sequence. The spacer in the bacterial CRISPR loci will not contain a PAM sequence, and will thus not be cut by the nuclease. However, the protospacer in the invading virus or plasmid will contain the PAM sequence, and will thus be cleaved by the Cas endonuclease. For editing genes, guide RNAs are synthesized to perform the function of recognizing gene sequences having a PAM sequence at the 3'-end. FIG. 1A shows the exemplified structure of crRNA.

The term "chimeric guide RNA" refers to a chimeric RNA molecule that integrates other RNA structures and modifications with conventional crRNA.

The term "caRNA" or "caged crRNA" refers to a kind of chimeric guide RNA at least one crRNA sequence and at least one additional direct repeat sequences. FIG. 1B shows an exemplified structure of caRNA having a spacer sequence flanked by two direct repeat sequences.

The term "csRNA" refers to a kind of chimeric guide RNA comprising at least one crRNA sequence and at least one small RNA species linked by a linker. The linker sequence generally is between 1 to 200 bases. FIG. 1C shows an exemplified structure of csRNA having a crRNA sequence linked with a truncated t-RNA.

The term "catRNA" refers to a kind of chimeric guide RNA comprising at least one crRNA sequence, at least one small RNA species and at least one additional direct repeat sequences. The small RNA species is linked to the crRNA sequence with a linker, which generally has a length between 1 to 200 bases. FIG. 1D shows an exemplified structure of catRNA having a a truncated t-RNA linked with a crRNA sequence followed by an additional direct repeat sequence.

The term "tracrRNA" refers to an associated trans-activating CRISPR RNA hybridizes with the direct repeats of crRNA, forming an RNA duplex that is cleaved and processed by endogenous RNase III and other unknown nucleases. Maturated crRNAs are then loaded onto effector protein complexes for target recognition and degradation. In type II CRISPR systems, the crRNA-tracrRNA hybrids complex with Cas9 to mediate interference.

The term "single guide RNA" or "sgRNA" refers to an artificially engineered RNA designed by fusing the crRNA and tracrRNA molecules into a "single-guide RNA" that, when combined with Cas9 protein, could find and cut the DNA target specified by the guide RNA.

The term "PAM" refers to protospacer adjacent motif that is a 2-6 base pair DNA sequence immediately following the DNA sequence targeted by the Cas endonuclease in the CRISPR bacterial adaptive immune system. PAM is a component of the invading virus or plasmid, but is not a component of the bacterial CRISPR locus. Cas protein will not successfully bind to or cleave the target DNA sequence if it is not followed by the PAM sequence. PAM is an essential targeting component (not found in bacterial genome) which distinguishes bacterial self from non-self DNA, thereby preventing the CRISPR locus from being targeted and destroyed by the endonuclease. Cas9 of *Francisella novicida* or *Streptococcus pyogenes* recognizes the canonical PAM sequence 5'-NGG-3', but has been engineered to recognize the PAM 5'-YG-3' (where "Y" is a pyrimidine), thus adding to the range of possible Cas9 targets. The Cpf1 nuclease of *Francisella novicida* recognizes the PAM 5'-TTTN-3' or 5'-YTN-3'.

The term "tRNA" refers to transfer RNA, an adaptor molecule composed of RNA, typically 76 to 90 nucleotides in length that serves as the physical link between the mRNA and the amino acid sequence of proteins. tRNA does this by carrying an amino acid to the protein synthetic machinery of a cell (ribosome) as directed by a three-nucleotide sequence (codon) in a messenger RNA (mRNA). As such, tRNAs are a necessary component of translation, the biological synthesis of new proteins in accordance with the genetic code.

The term "pre-tRNA" refers to the precursor RNA of tRNA. The precursor tRNA can be cleaved to produce tRNA molecules from the 5' leader or 3' trail sequences. Cleavage enzymes include Angiogenin, Dicer, RNase Z and RNase P. Certain pre-tRNAs contain a 5'methylguanosine cap and 3' Poly-A tail. "Pre-tRNA" can be in a truncated form, in which the acceptor stem region only has a length of about 5 bp, while the intact pre-tRNA generally has a length of about 7-9 bp in the acceptor stem region.

The term "gene editing" refers to a type of genetic engineering in which DNA is inserted, deleted, modified or replaced in the genome of a living organism. In 2018, the common methods for such editing use engineered nucleases, or "molecular scissors". These nucleases create site-specific double-strand breaks at desired locations in the genome. The induced double-strand breaks are repaired through non-homologous end-joining (NHEJ) or homologous recombination (HR), resulting in targeted mutations ('edits'). As of 2015 four families of engineered nucleases were used: meganucleases, zinc finger nucleases (ZFNs), transcription activator-like effector-based nucleases (TALEN), and the clustered regularly interspaced short palindromic repeats (CRISPR/Cas9) system.

The term "pooled gRNAs" or "a gRNA pool" or "a pool of gRNAs" are used interchangeably, refers to a combination of individually expressed gRNAs targeting the same or different loci located in the same or different DNA sequences. In the context of the present application, crRNA, caRNA, csRNA and catRNA all can be presented in the form of a pool.

The term "arrayed gRNAs" or "a gRNA array" or "an array of gRNAs" are used interchangeably, refers to an array of gRNAs specific for the same or different loci located in the same or different DNA sequences, expressed from or processed from a single RNA transcript. In the context of the present application, crRNA, caRNA, csRNA and catRNA all can be presented in the form of an array.

The term "small RNA" refers to RNA species that are <200 nt (nucleotide) in length, and are usually non-coding RNA molecules. The small RNAs usually resemble tRNA in harboring different stem-loop or hairpin structures or terminal modifications that confer RNases resistant property. The small RNA species herein include transfer RNA (tRNA), microRNA (mirRNA), Piwi-interacting RNA (piRNA), small interfering RNA (siRNA), small nucleolar RNA (snoRNA), tRNA-derived small RNA (tsRNA), small rDNA-derived RNA (srRNA), long non-coding RNA (lncRNA), small nuclear RNA (U-RNA), short-hairpin RNA (shRNA), pre-tRNA as well as messenger RNA (mRNA). In the present invention, the small RNA can be used alone or in combination when fused to the crRNA sequence, and the small RNA can be the same or different in one chimeric guide RNA. Further, the small RNA can be used in truncated forms.

The term "mRNA" refers to messenger RNA, a large family of RNA molecules that convey genetic information from DNA to the ribosome, where they specify the amino acid sequence of the protein products of gene expression. Following transcription of primary transcript mRNA (known as pre-mRNA) by RNA polymerase, processed mature mRNA is translated into a polymer of amino acids: a protein, as summarized in the central dogma of molecular biology. Eukaryotic pre-mRNA, requires extensive processings that confer RNases resistance as well as initiate translation. The processings includes 5'methylguanosine capping (5' cap), 3'Polyadenylation (3' Poly-A) and editing, which are also features of pre-tRNAs.

As used herein, "functional variant" of Cpf1 refers to a biologically active variant, i.e., it comprises one or more functional properties of Cpf1. In the context of the present invention, a "variant" of Cpf1 has at least 60%, at least 70%, at least 80%, at least 85%, at least 90%, at least 92%, at least 94%, at least 96%, at least 98%, at least 99% sequence identity with the amino acid sequence of Cpf1. The "variant" of Cpf1 also encompasses those has at least 80%, at least 85%, at least 90%, at least 92%, at least 94%, at least 96%, at least 98%, least 99% sequence identity with the amino acid sequence of RuvC of Cpf1. Functional variant of a Cpf1 protein can be obtained by mutation in a wild-type Cpf1 protein, which result in the addition, deletion or replacement of one or more amino acids. The mutation method is well known in the art, such as random or targeted mutagenesis. For example, dead LbCpf1 is a functional variant of LbCpf1, which comprises a D832A mutation resulting in the loss of its DNA endonuclease catalytic activity. "functional variant" of Cpf1 also encompasses chimeric Cpf1 proteins which comprising a first fragment from a first Cpf1 protein and a second fragment from a second Cpf1 protein, wherein the first and the second Cpf1 proteins are different.

The term "CARs" or "chimeric antigen receptors" refers to engineered receptors which graft an arbitrary specificity onto an immune effector cell (T cell). Typically, these receptors are used to graft the specificity of a monoclonal antibody onto a T cell, with transfer of their coding sequence facilitated by retroviral vectors. The receptors are called chimeric because they are composed of parts from different sources.

The term "CAR T cell" or "chimeric antigen receptor T cell" refers to engineered T cells with chimeric antigen receptors which have pre-defined specificity towards selected targets. Once encountered with targets, for example cancer cells, CAR T cells destroy the cancer cells through mechanisms such as extensive stimulated cell proliferation, increasing the degree to which the cell is toxic to other living cells i.e. cytotoxicity, and by causing the increased production of factors that are secreted from cells in the immune system that have an effect on other cells in the organism.

The term "antigen" or "Ag" is defined as a molecule that provokes an immune response. This immune response may involve either antibody production, or the activation of specific immunologically-competent cells, or both. A skilled artisan will understand that any macromolecule, including virtually all proteins or peptides, can serve as an antigen. In addition, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated or synthesized or can be derived from a biological sample. Such a biological sample can include, but is not limited to a tissue sample, a tumor sample, a cell or a biological fluid.

Engineered Chimeric Guide RNA

The present invention provides an engineered chimeric guide RNA comprising: (1) at least one crRNA sequences, and (2) at least one additional direct repeat sequences or small RNA species or both, wherein the crRNA sequence is capable of hybridizing with a target locus of interest, and the additional direct repeat sequence and/or the small RNA species confers increased stability of the chimeric guide RNA.

In one specific embodiment, the engineered chimeric guide RNA is a caRNA comprising at least one crRNA sequence and at least one additional direct repeat sequences. In one specific embodiment, the engineered chimeric guide RNA is a csRNA comprising at least one crRNA sequences and at least one small RNA species. In a further embodiment, the engineered chimeric guide RNA is a catRNA comprising at least one crRNA sequences and at least one direct repeat sequences and small RNA species.

In one embodiment, the small RNA species are selected from the group consisting of transfer RNA (tRNA), microRNA (mirRNA), Piwi-interacting RNA (piRNA), small interfering RNA (siRNA), small nucleolar RNA (snoRNA), tRNA-derived small RNA (tsRNA), small rDNA-derived RNA (srRNA), long non-coding RNA (ln-cRNA), small nuclear RNA (U-RNA), short-hairpin RNA (shRNA), pre-tRNA as well as messenger RNA (mRNA). These small RNA species have structures in common, such as stem-loop or hairpin structures or terminal modifications.

Transfer RNAs (tRNAs) are the most stable RNA molecules because they harbor multiple hairpins (or stem loops) and 3' trailer tail structures that impart resistance to various RNase molecules. Precursor-tRNAs (pre-tRNAs) are occasionally capped with methylguanosine at their 5' termini (Vakiloroavaei A et al., 2017). A recent study in *Saccharomyces cerevisiae* found that methylguanosine cap structures protect pre-tRNAs from degradation by RNases, and the cap structures likely act as a shield to protect pre-tRNA during the maturation process (Ohira T et al., 2016). Pre-tRNA is processed into mature tRNA by removal of the 5' leader sequence with RNase P followed by RNase Z cleavage at the 3' end. As the 7~9-base pair acceptor stem structure is critical for RNase P recognition and cleavage, disruption of the acceptor stem will limit leader cleavage and tRNA maturation by RNase P (Brillante N et al., 2016; Werner et al., 1998). In addition, because RNase Z accepts only tRNA precursors with mature 5' ends, hindering RNase P processing will also cause RNase Z cleavage failure (Kunzmann A et al., 1998). Thus, the inventors engineered an RNase-resistant catRNA comprising truncated pre-tRNA with a 5' cap and a 3' tail, demonstrating that robust gene editing in mammalian cells can be achieved.

In one embodiment, said other small RNA species can be in truncated forms, as long as such truncation does not adversely affect the activity of the chimeric guide crRNA compared to the corresponding intact form. For example, the truncated form of pre-tRNA that comprises a truncated stem region can be used in the present invention. Specifically, compared to the intact pre-tRNA which has a length of about 7-9 bp in the acceptor stem region, the truncated pre-tRNA only has a length of about 5 bp in the same acceptor stem region.

If multiple crRNAs or small RNA species are present within one chimeric guide RNA, they can be the same or different from each other. The crRNA sequences and small RNA species can be arranged in any order.

In another embodiment, the engineered chimeric guide RNA further comprises one or more elements selected from untranslated region (UTR), poly-A and 5' methylguanosine cap. These elements provide protection of the chimeric RNA from RNases, thus increase the half-life of the chimeric RNA.

In a specific embodiment, the engineered chimeric guide RNA is a caRNA comprising one crRNA and one additional direct repeat. In another specific embodiment, the engineered chimeric guide RNA is a csRNA comprising one crRNA and one small RNA such as tRNA or pre-tRNA or a truncated form thereof. Yet in another specific embodiment, the engineered chimeric guide RNA is a catRNA comprising one crRNA, one additional direct repeat sequence and one small RNA, wherein the small RNA may be tRNA or pre-tRNA or a truncated form thereof.

The engineered chimeric guide RNA may target one or more loci, wherein said loci are presented in same or different DNA sequences. For example, a plurality of engineered chimeric guide RNAs according to the present invention can be used together in the form of a pool, with each chimeric guide RNA transcribed from an independent RNA molecule and targets the same locus in one gene, or different loci in one gene, or different loci in different genes. Further, the engineered chimeric guide RNA according to the present invention can also be used in the form of an array, which is transcribed from a single RNA molecule and comprises multiple crRNAs and/or one or more direct repeat sequences and/or one or more small RNA species, wherein said multiple crRNAs target the same locus in one gene, or different loci in one gene, or different loci in different genes.

The crRNA contained in the chimeric guide RNA comprises a spacer sequence, said spacer sequence has a length from 10 to 30 bp, preferably about 16-24 bp. For example, the spacer is 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp or 30 bp in length. In certain embodiments, when the Cpf1 is LbCpf1, it requires at least 16 nt of spacer sequence to achieve detectable DNA cleavage and a minimum of 17 nt of spacer sequence to achieve efficient DNA cleavage in vitro.

The engineered chimeric guide RNA according to the present application hybridizes to a target sequence, wherein said target sequence is 3' of a Protospacer Adjacent Motif (PAM). Preferably, the PAM comprises a 5' T-rich motif.

For example, when the PAM sequence is TTN and N is A/C/G or T, the Cpf1 protein is FnCpf1; when the PAM sequence is TTTN and N is A/C or G, the Cpf1 protein is PaCpf1, LbCpf1 or AsCpf1.

The CRISPR/Cpf1 System

Clustered Regularly Interspaced Short Palindromic Repeats from *Prevotella* and *Francisella* 1 or CRISPR/Cpf1 is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

Figure 2:
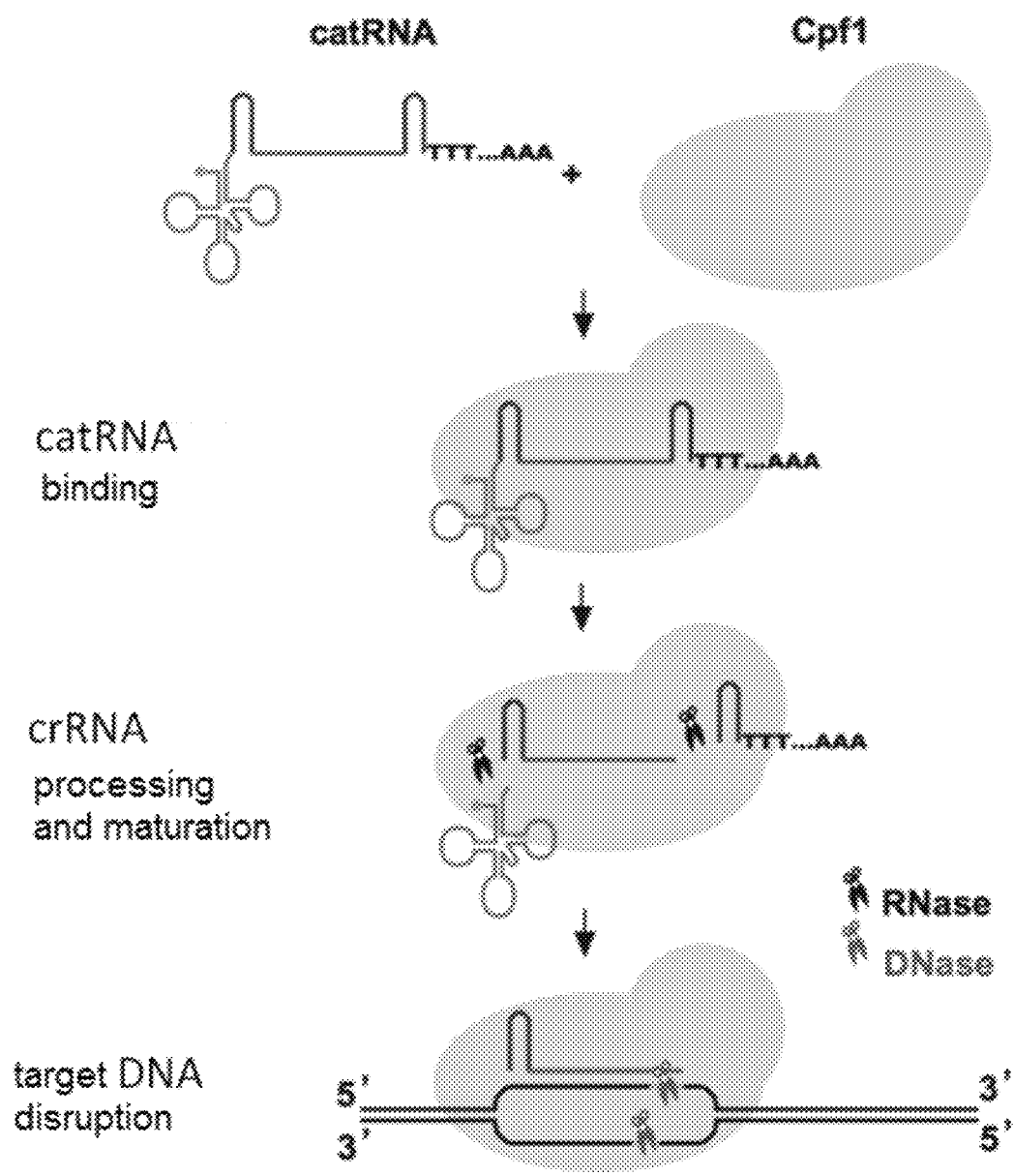
FIG. 2: Schematic flowchart of target DNA disruption using the catRNA according to the present invention.

FIG. 2 is a schematic flowchart illustrating the catRNA according to the present invention works. Briefly, the catRNA binds to the Cpf1 protein to form a complex, and then under the actions of RNases, the Cpf1 protein processes catRNA by cutting off the small RNA species such as truncated pre-tRNA as well as the additional direct repeat sequences with poly T and/or poly A. A processed mature crRNA still binding with the Cpf1 protein is obtained, which then hybridizes with the target sequence by base pairing and cuts the target sequence with the help of DNases.

Cas9 requires two RNA molecules to cut DNA while Cpf1 needs one. The proteins also cut DNA at different places, offering researchers more options when selecting an editing site. Cas9 cuts both strands in a DNA molecule at the same position, leaving behind blunt ends. Cpf1 leaves one strand longer than the other, creating sticky ends. The sticky ends aid in the incorporation of new sequences of DNA, making Cpf1 more efficient at gene introductions than Cas9. Although the CRISPR/Cas9 system can efficiently disable genes, it is challenging to insert genes or generate a knock-in. Cpf1 lacks tracrRNA, utilizes a T-rich PAM and cleaves DNA via a staggered DNA DSB.

In summary, important differences between Cpf1 and Cas9 systems are that Cpf1 is able to:
  recognize different PAMs, enabling new targeting possibilities;
  create 4-5 nt long sticky ends, instead of blunt ends produced by Cas9, enhancing the efficiency of genetic insertions and specificity during NHEJ or HDR;
  cut target DNA further away from PAM, further away from the Cas9 cutting site, enabling new possibilities for cleaving the DNA.

Thus, the present invention provides a CRISPR/Cpf1 system comprising:
  (a) one or more engineered chimeric guide RNAs according to the present application, or one or more polynucleotide sequences encoding the engineered chimeric guide RNAs according to the present application; and
  (b) a Cpf1 protein or a functional variant thereof, or one or more polynucleotide sequences encoding the Cpf1 protein or a functional variant thereof.

When the components (a) and (b) are polynucleotide sequences, they may present in the same or different vectors.

The system may further comprise $Mg^{2+}$, preferably at a concentration from about 1 mM to about 15 mM. The presence of $Mg^{2+}$ forms a complex with the endonuclease and stabilizes the latter to enchance the hydrolysis activity.

The Cpf1 protein may be a wild type Cpf1 protein or a functional Cpf1 variant thereof which maintains the endonuclease activity of the wild type Cpf1 protein, such as a functional Cpf1 mutant or a chimeric Cpf1 protein. A functional Cpf1 variant can be obtained by one skilled in the art using any known methods such as directed or random mutagenesis or DNA recombination. The effects of the obtained Cpf1 variant can be verified by well known methods such as DNA cleavage analysis.

The Cpf1 protein or a functional variant thereof may derived from an organism selected from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium* and *Acidaminococcus*. Preferably, the Cpf1 protein or a functional variant thereof is derived from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis*1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma termitum, Eubacterium eligens, Moraxella bovoculi237, *Leptospira inadai*, Lachnospiraceae bacterium ND2006, *Porphyromonas crevioricanis*3, *Prevotella disiens* and *Porphyromonas macacae*. Most preferably, the Cpf1 protein or a functional variant thereof is derived from *Prevotella albensis* (PaCpf1), Lachnospiraceae bacterium ND2006 (LbCpf1), *Francisella tularensis* subsp. *novicida* (FnCpf1), or *Acidaminococcus* sp. BV3L6 (AsCpf1).

The Cpf1 mutant may be used to expand the application of this protein. For example, utility of the commonly used AsCpf1 and LbCpf1 is limited by their requirement of a TTTN protospacer adjacent motif (PAM) in the DNA substrate. To address this limitation, engineered AsCpf1 variants carrying the mutations S542R/K607R and S542R/K548V/N552R had been developed, which recognize TYCV and TATV PAMs, respectively, with enhanced activities in vitro and in human cells. Introducing the identified PAM-interacting mutations at their corresponding positions in LbCpf1 similarly altered its PAM specificity. And LbCpf1 was engineered to recognize TYCV and TATV PAMs by introducing the mutations G532R/K595R and G532R/K538V/Y542R, respectively Together, these variants increase the targeting range of Cpf1 by approximately threefold in human coding sequences to one cleavage site per ~11 bp. Detailed description of these variants can be found for example in International Patent Publication WO2017184768A1, the entire content of which is incorporated herein by reference.

The chimeric Cpf1 protein comprises a first fragment from a first Cpf1 protein and a second fragment from a second Cpf1 protein, and wherein the first and second Cpf1 proteins are different.

In one embodiment, the Cpf1 protein or a functional variant thereof comprises one or more nuclear localization signals.

The present invention also encompasses a cell or cell line or progeny thereof comprising the above system according to the present invention Gene Editing Method Currently, there are generally four systems for gene editing, namely meganuclease-based system, zinc finger nuclease-based system (ZFNs), transcription activator-like effector nucleases (TALENs) system and CRISPR system.

Meganucleases, found commonly in microbial species, have the unique property of having very long recognition sequences (>14 bp) thus making them naturally very specific. However, there is virtually no chance of finding the exact meganuclease required to act on a specific DNA sequence. To overcome this challenge, mutagenesis and high throughput screening methods have been used to create meganuclease variants that recognize unique sequences. Others have been able to fuse various meganucleases and create hybrid enzymes that recognize a new sequence. Yet others have attempted to alter the DNA interacting amino acids of the meganuclease to design sequence specific meganucleases in a method named rationally designed meganuclease.

Zinc finger proteins (ZFNs) recognize target DNA in a modular fashion: each protein consists of at least three zinc finger domains, and a single zinc finger domain interacts with a 3-bp sequence, making them ideal programmable sequence-specific DNA-binding proteins TALENs emerged as a competitive alternative to ZFNs in 2011. Unlike zinc fingers, each repeat domain in TALE proteins recognizes a single base. Four different repeat domains can be mixed and matched to create new DNA-binding proteins, which can be linked to the FokI domain to create a new class of programmable target DNA nucleases. These molecules enable precise targeting and cutting at a specific genomic locus to generate double-strand breaks (DSBs) followed by non-homologous end joining (NHEJ) or homology-directed repair (HDR)-mediated repair, thereby enabling precise genome editing.

Studies using ZFN and TALEN have led to important scientific discoveries and therapeutic development. In fact, a ZFN-based treatment of HIV that disables the HIV co-receptor C—C chemokine receptor type 5 (CCR5) in human primary T cells is currently in clinical trials and has shown great promise. However, the recognition of the target DNA sequence by these protein-based genome engineering systems is determined by protein sequences. Tedious and complex protein engineering and optimization are therefore required for each specific target DNA sequence and delivering many of these proteins into cells for simultaneous multiplexed genetic manipulation is challenging. Given these difficulties, their use for large-scale genomic manipulation or genetic screens has been limited.

As mentioned above, CRISPRs are genetic elements that bacteria use as a kind of acquired immunity to protect against viruses. They consist of short sequences that originate from viral genomes and have been incorporated into the bacterial genome. Cas (CRISPR associated proteins) processes these sequences and cut matching viral DNA sequences. By introducing plasmids containing Cas genes and specifically constructed CRISPRs into eukaryotic cells, the eukaryotic genome can be cut at any desired position.

Thus, the present invention provides a method of editing a target locus of interest, comprising delivering to said locus a CRISPR/Cpf1 system comprising:
  (a) one or more engineered chimeric guide RNAs according to the present application, or one or more polynucleotide sequences encoding the engineered chimeric guide RNAs according to the present application; and
  (b) a Cpf1 protein or a functional variant thereof, or one or more polynucleotide sequences encoding the Cpf1 protein or a functional variant thereof.

The target locus of interest is within a cell, for example a eukaryotic cell, such as an animal, human or plant cell. In another embodiment, the target locus is comprised in a DNA molecule in vitro The present invention also provides a method of altering expression of at least one target gene, comprising delivering into a cell comprising said target gene a CRISPR/Cpf1 system comprising:
  (a) one or more engineered chimeric guide RNAs according to the present application, or one or more polynucleotide sequences encoding the engineered chimeric guide RNAs according to the present application; and
  (b) a Cpf1 protein or a functional variant thereof, or one or more polynucleotide sequences encoding the Cpf1 protein or a functional variant thereof.

The cell is a eukaryotic cell, such as an animal, human or plant cell.

The components (a) and (b) of the CRISPR/Cpf1 system can be delivered together or separately. For example, when the components (a) and (b) are polynucleotides, they can be delivered in the manner of:
  a single vector containing two or more expression cassettes as follows: promoter-Cpf1 coding nucleic acid molecule-terminator; promoter-gRNA1-terminator; promoter-gRNA2-terminator; promoter-gRNA(N)-terminator (up to size limit of vector); or
  double vectors, wherein vector 1 contains one expression cassette for driving the expression of Cpf1: promoter-Cpf1 coding nucleic acid molecule-terminator; vector 2 contains one more expression cassettes for driving the expression of one or more chimeric guide RNAs according to the present invention: promoter-gRNA1-terminator, promoter-gRNA(N)-terminator (up to size limit of vector).

In addition to the single and double virus vector approaches described above, an additional vector can be used to deliver a homology-direct repair template.

The CRISPR/Cas system can be delivered by any method known in the art, for example, by directly applying said system to human cells by transfection with a plasmid that encodes Cas and sgRNA. The viral delivery of CRISPR components has been extensively demonstrated using lentivirus and retrovirus. Gene editing with CRISPR encoded by non-integrating virus, such as adenovirus and adenovirus-associated virus (AAV), has also been reported. Recent discoveries of smaller Cas proteins have enabled and enhanced the combination of this technology with vectors that have gained increasing success for their safety profile and efficiency, such as AAV vectors. Due to their relatively low immunogenicity, AAVs are commonly chosen for in vivo gene delivery in somatic gene therapy. CRISPR delivery via Cas ribonucleoproteins (RNP) also exhibited efficient gene editing in human cells. More examples of delivering methods for the CRISPR/Cpf1 system can be found in U.S. Pat. No. 9,790,490B2, the entire content of which is incorporated herein by reference.

Electroporation is so far the most oftenly used method for delivering genetic materials including DNA, RNA and protein into T cells. Electroporation is a microbiology technique in which an electrical field is applied to cells in order to increase the permeability of the cell membrane, allowing chemicals, drugs, DNA, RNA or protein to be introduced into the cell.

Due to the lower transduction efficiency of viruses, including lentivirus, retrovirus or adenovirus into T cells, as well as the toxicity associated with prolonged CRISPR/Cas expression, electroporation has been used for high efficiency and low toxicity gene manipulations in T cells.

Compared with DNA that might be seen as foreign genetic material or DNA damages, which will initiate apoptosis pathway as results in cell death, electroporation of RNA and protein are less toxic and more tolerable to T cells.

The process for electroporation used in the present invention is briefly described as follows:
1. Genetic materials are prepared before mixing with target cells, such as a T cell. T cell can be naïve or activated T cells.
   If DNA encoding the Cpf1 protein and chimeric guide RNA is used, electroporation of DNA is performed by a single electroporation;
   If Cpf1 mRNA is used, sequential or double electroporation is used. Electroporation of Cpf1 mRNA is followed by the electroporation of a chimeric guide RNA. The interval between the two electroporations is within 24 hours.
   If Cpf1 protein and chimeric guide RNAs are used, pre-incubation of Cpf1 protein with chimeric guide crRNAs is performed before mixing with target cells.
2. Mixing prepared genetic materials with target cells;
3. Perform electroporation with electroporators.
4. Transfer electroporated cells into culture media and culture for sufficient time under suitable conditions.

Engineered T Cells

T cells can be engineered to express modified TCRs (so-called TCR therapies) or protein-fusion-derived chimeric antigen receptors (CARs) that have enhanced antigen specificity. These approaches could overcome the fundamental limitations associated with central and peripheral tolerance and generate T cells that will be more efficient at targeting tumours without the requirement for de novo T-cell activation in the patient.

Genetically modified TCR therapies are based on altering T-cell specificity through the expression of specific TCR α and β chains, which mediate the antigen-recognition process. The tumour-specific TCR α and β chains are identified, isolated and cloned into transduction vectors and transduction of T cells creates tumour-antigen-specific T cells.

Chimeric antigen receptors (CARs) combine both antibody-like recognition with T-cell-activating function. They are composed of an antigen-binding region, typically derived from an antibody, a transmembrane domain to anchor the CAR to the T cell, and one or more intracellular signalling domains that induce persistence, trafficking and effector functions in transduced T cells. Sequences used to define the antigen-targeting motif for a CAR are typically derived from a monoclonal antibody, but ligands and other receptors can also be used.

Figure 10:
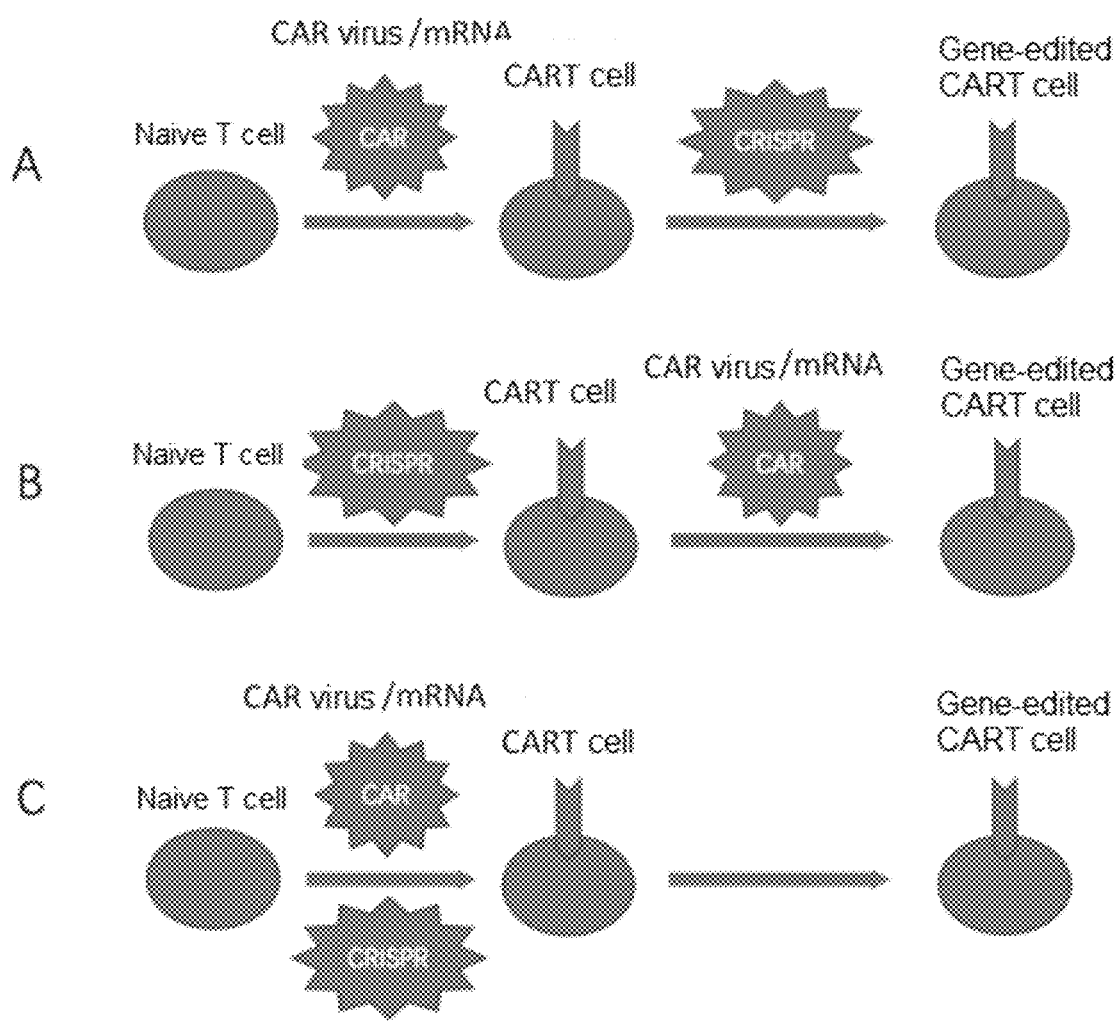
FIG. 10: Schematic representation of the method for preparing genetically modified therapeutic T-cells. A: Naïve T cells are transduced with CAR and then gene edited by CRISPR; B: Naïve T cells are gene edited by CRISPR followed by CAR transduction; C: Gene editing and CAR transduction are executed at the same time innaïve T cells.

When preparing gene edited CAR T cells, the transduction of T cells and gene editing can be performed in any order. Specifically, the transduction of T cells can be carried at before (FIG. 10A), after (FIG. 10B) or at the same time (FIG. 10C) with gene editing by the CRISPR system.

Currently, most CAR T clinical trials utilize autologous T cells and might therefore be hampered by the poor quality and quantity of T cells and by the time and expense of manufacturing autologous T cell products. CAR T cell therapy could substantially benefit from allogeneic universal donor T cells, as "off-the-shelf" cells could greatly increase the number of patients who could be treated by a single CAR T cell product. However, endogenous TCR on allogeneic T cells may recognize the alloantigens of the recipient, leading to graft-versus-host disease (GVHD); furthermore, the expression of HLA on the surface of allogeneic T cells causes rapid rejection by the host immune system. In this context, ZFNs and TALENs have been used to knock out endogenous T cell receptor genes in T cells, which could prevent unwanted graft-versus-host reactivity. Genome-editing strategies could also be used to prevent or delay the rejection of CAR T cells by the recipient's immune system by eliminating or decreasing the expression of histocompatibility antigens on the donor T cells. Future CAR T cell therapies could benefit from combined modification of endogenous TCR genes, histocompatibility genes, and components of signaling pathways.

In a previous study, CRISPR/Cas9 system had been used to simultaneously disrupt multiple genomic loci. CAR T cells deficient in the expression of endogenous T cell receptor (TCR) and HLA class I (HLA-I) were generated, which can be used as universal CAR T cells.

A potential issue for TCR/HLA is the activation of NK cells, which may cause quick rejection of these cells. Another approach is that the CD52 gene was also disrupted using TALEN to allow the administration of engineered T-cells following an alemtuzumab-based lymphodepleting therapy.

However, gene disruption efficiency of TCR/CD52 with TALEN is very low (30%), thus limiting its usage for large-scale manufacture process.

In the current invention, we provided a more efficient method for preparing universal CAR T cells. Specifically, the present invention provides a method of preparing engineered T-cells, comprising the steps of genetically modifying the T cells by introducing into the cells and/or expression in the T cells a system comprising at least:
   a Cpf1 protein or a functional variant thereof, or one or more polynucleotide sequences encoding the Cpf1 protein or a functional variant thereof; and
   one or more engineered chimeric guide RNAs according to the present application, or one or more polynucleotide sequences encoding the engineered chimeric guide RNAs according to the present application.

In one embodiment, the method of preparing engineered T-cells further comprises a step of (b) expanding the engineered T cells in vitro.

In one embodiment, the method of preparing engineered T-cells further comprises a step of (b) transducing chimeric antigen receptors (CARs) into the T cells. In particular, the step (b) is performed before, after or at the same time with the step (a) of genetically modifying the T cells.

In a specific embodiment, the T cells are derived from peripheral blood mononuclear cell (PBMC) or cord blood. Preferably, the T cells are derived from inflammatory T-lymphocytes, cytotoxic T-lymphocytes, regulatory T-lymphocytes or helper T-lymphocytes, in particular CD4+T-lymphocytes and/or CD8+T-lymphocytes.

The inventors surprisingly found that the above method according to the present invention achieved highly efficient gene disruption (~90%) at TCR and CD52 loci with engineered chimeric guide RNAs.

The present invention also provides the engineered T cells, in particular allogeneic T cells prepared according to the above method of the present invention.

In a further embodiment, the engineered T cells further comprise exogenous recombinant polynucleotides encoding CARs for specific cell recognition.

In particular, the engineered T cells according to the present invention has a wide application, for example used as an active ingredient in a pharmaceutical composition product, ideally as an "off the shelf" product, for treating or preventing conditions such as cancer, infections or autoimmune disease.

The conditions that can be treated by the engineered T cells include but not limited to cancer, infections or autoimmune diseases. Cancers that can be treated with engineered T cells include but not limited to acute lymphocytic leukemia (ALL), chronic lymphocytic leukemia (CLL), acute myelogenous leukemia (AML), breast cancer, lung cancer, colorectal cancer, gastric cancer, pancreatic caner, ovarian cancer, metastatic adenocarcinomas, liver metastases, sarcoma, osteosarcoma, neuroblastoma, melanoma, mesothelioma, glioblastoma, glioma, malignant glioma, hepatocellular, non-small cell lung caner (NSCLC), ganglioneuroblastoma, brain cancer, renal cancer and prostate cancer. Infectious diseases that can be treated with engineered T cells include but not limited to infection caused by virus, bacteria, fungi and parasites. Autoimmune diseases that can be treated with engineered T cells include but not limited to type I diabetes, celiac disease, Graves' disease, inflammatory bowel disease, multiple sclerosis, psoriasis, rheumatoid arthritis, Addison's disease, Sjögren's syndrome, Hashimoto's thyroiditis, Myasthenia gravis, Vasculitis, Pernicious anemia and systemic lupus erythematosus.

The cancer is eliminated by the engineered T cells through the recognition of specific tumor antigens. Herein the tumor antigen is selected from the group consisting of TSHR, CD19, CD123, CD22, CD30, CD171, CS-1, CLL-1, CD33, EGFRVIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-1 1Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gplOO, bcr-abl, tyrosinase, EphA2, Fucosyl GMI, sLe, GM3, TGS5, HMWMAA, o-acetyl-GD2, Folate receptor beta, TEM1/CD248, TEM7R, CLDN6, GPRC5D, CXORF61, CD97, CD 179a, ALK, Polysialic acid, PLAC1, Glo-boH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B 1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1, and any combination thereof.

EXAMPLES

The following examples are only provided for the purpose of illustration, and will not limit the scope of the present invention in any way.

Example 1: Efficient Gene Disruption with Various gRNAs

All crRNA, caRNA, csRNA and catRNA used were synthesized using the HiScribe™ T7 High Yield RNA Synthesis Kit (NEB), and then cloned into pcDNA3.1 plasmids driven by U6, T7 or EF1a promoters respectively. To initiate efficient transcription under the U6 and T7 promoters, a single "G" nucleotide was added in front of all the crRNA, caRNA, csRNA and catRNA sequences.

In all examples, crRNA comprises one spacer sequence and one direct repeat sequence (FIG. 1A); caRNA comprises an additional direct repeat sequence linked with said crRNA (FIG. 1B); csRNA comprises a truncated pre-tRNA linked with said crRNA (FIG. 1C); and catRNA comprises a truncated pre-tRNA linked with said crRNA followed by the additional direct repeat sequence (FIG. 1D).

The sequences of various gRNAs used in the examples are listed in the following Table 1, wherein bold letters indicate the direct repeat sequence, the italic and underlined letters indicate the sequence of truncated pre-tRNA, and the underlined letters indicate the spacer sequence.

TABLE 1

Sequences of various gRNAs used in this example.

| Name | gRNA sequences |
|---|---|
| DNMT1-crRNA | GAATTTCTACTAAGTGTAGATCTGATGGTCCATG TCTGTTACTCTTTTTT (SEQ ID NO: 1) |
| VEGFa-crRNA | GAATTTCTACTAAGTGTAGATCTAGGAATATTGA AGGGGGCAGGTTTTTT (SEQ ID NO: 2) |
| GRIN2b-crRNA | GAATTTCTACTAAGTGTAGATGTGCTCAATGAAA GGAGATAAGGTTTTTT (SEQ ID NO: 3) |
| DNMT1-caRNA | GAATTTCTACTAAGTGTAGATCTGATGGTCCATG TCTGTTACTCAATTTCTACTAAGTGTAGATTTTT TTAAAAAA (SEQ ID NO: 4) |
| VEGFa-caRNA | GAATTTCTACTAAGTGTAGATCTAGGAATATTGA AGGGGGCAGGAATTTCTACTAAGTGTAGATTTTT TTAAAAAA (SEQ ID NO: 5) |
| GRIN2b-caRNA | GAATTTCTACTAAGTGTAGATGTGCTCAATGAAA GGAGATAAGGAATTTCTACTAAGTGTAGATTTTT TTAAAAAA (SEQ ID NO: 6) |
| DNMT1-csRNA | *GCCAGTGGTCTAGTGGTAGAATAGTACCCTGCCA CGGTACAGACCCGGGTTCGATTCCCGGCTGGAA*TAATTTCTACTAAGTGTAGATCTGATGGTCCATG TCTGTTACTCTTTTTT (SEQ ID NO: 7) |

TABLE 1-continued

Sequences of various gRNAs used in this example.

| Name | gRNA sequences |
|------|----------------|
| VEGFa-csRNA | GCCAGTGGTCTAGTGGTAGAATAGTACCCTGCCA CGGTACAGACCCGGGTTCGATTCCCGGCTGGAAA TAATTTCTACTAAGTGTAGATCTAGGAATATTGA AGGGGGCAGGTTTTTT (SEQ ID NO: 8) |
| GRIN2b-csRNA | GCCAGTGGTCTAGTGGTAGAATAGTACCCTGCCA CGGTACAGACCCGGGTTCGATTCCCGGCTGGAAA TAATTTCTACTAAGTGTAGATGTGCTCAATGAAA GGAGATAAGGTTTTTTAAAAAA (SEQ ID NO: 9) |
| DNMT1-catRNA | GCCAGTGGTCTAGTGGTAGAATAGTACCCTGCCA CGGTACAGACCCGGGTTCGATTCCCGGCTGGAAA TAATTTCTACTAAGTGTAGATCTGATGGTCCATG TCTGTTACTCAATTTCTACTAAGTGTAGATTTTT TTAAAAAA (SEQ ID NO: 10) |
| VEGFa-catRNA | GCCAGTGGTCTAGTGGTAGAATAGTACCCTGCCA CGGTACAGACCCGGGTTCGATTCCCGGCTGGAAA TAATTTCTACTAAGTGTAGATCTAGGAATATTGA AGGGGGCAGGAATTTCTACTAAGTGTAGATTTTT TTAAAAAA (SEQ ID NO: 11) |
| GRIN2b-catRNA | GCCAGTGGTCTAGTGGTAGAATAGTACCCTGCCA CGGTACAGACCCGGGTTCGATTCCCGGCTGGAAA TAATTTCTACTAAGTGTAGATGTGCTCAATGAAA GGAGATAAGGAATTTCTACTAAGTGTAGATTTTT TTAAAAAA (SEQ ID NO: 12) |

The nucleotide sequence of LbCpf1 was amplified from Lachnospiraceae bacterium ND2006 and cloned into a pcDNA3.1 plasmid.

HEK293T cells (ATCC) were cultured in DMEM (Life Technologies, Carlsbad, CA, USA) supplemented with 10% FBS (Omega Scientific) and 25 mM Hepes. Cells were transfected in 6-well plates at 70% confluency with 2 μg of plasmid encoding LbCpf1 alone (control) or in combination with 2 μg of plasmid encoding various gRNAs using Lipofectamine 3000 (Life Technologies). These plasmids encoding gRNAs carry crRNAs targeting respectively the DNMT1, VEGFa and GRIN2b genes driven by a U6 polymerase III (Pol III) promoter or an EF1a polymerase II (Pol II) promoter. Cells were harvested for genomic DNA extraction 72 hours after DNA transfection. Specific knock-outs in DNMT1, VEGFa and GRIN2b genes were measured with TIDE online software.

Figure 3:
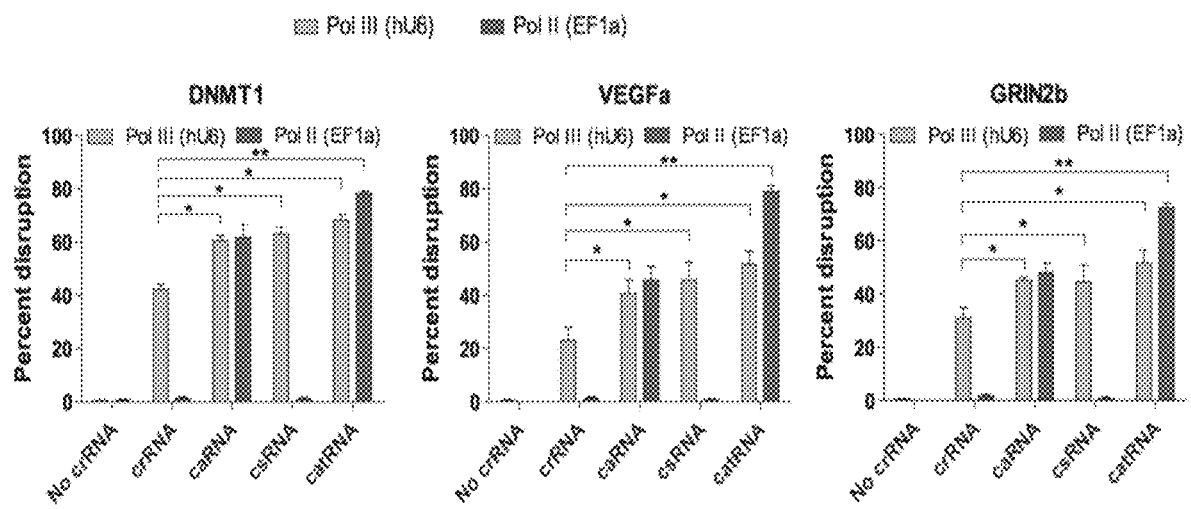
FIG. 3: Gene disruption efficiency with a single guide RNA in eukaryotic cells targeting the DNMT1 (A), VEGFa (B) or GRIN2b (C) gene. Bar, SE. n=3. *, P<0.05, , P<0.01, *, P<0.001, ****, P<0.0001 determined by the Mann-Whitney test.

The measured gene disruption efficiency results are shown FIG. 3. It was found that when the tested crRNA, caRNA, csRNA and catRNA are under the control of a pol III promoter, the gene disruption efficiencies obtained from caRNAs targeting DNMT1, VEGFa and GRIN2b genes (60.7%, 38.0%, and 47.3%, respectively) were significantly higher than those obtained from crRNA (42.1%, 23.2%, and 32.1%, respectively). csRNAs showed disruption efficiencies comparable to those of caRNAs in all three genes. Such significant increase was also observed when catRNAs were used. As shown in FIG. 3, the catRNAs efficiently disrupted DNMT1, VEGFa and GRIN2b genes with efficiencies reaching 68.3%, 51.6% and 51.7%, respectively.

It was also noted that catRNAs driven by the pol II promoter demonstrated a significantly increased efficiency compared to that driven by the pol III promoter against the tested three genes. The inventors also observed a trend towards higher efficiency using Pol-II caRNAs, although it was not comparable to those of catRNAs in this experiment.

This difference between caRNAs or catRNAs transcribed from pol II and pol III promoters were resulted from the presence of the 5' cap and 3' poly-A tail structures, which were only existed in the case of pol II promoter. The 5' cap and 3' poly-A tail structures provide protection against exo-RNases until Cpf1 cutting the additional direct repeat sequence off, thus conferring relatively higher stability and a much longer half-life, thereby enhanced gene editing efficiency.

However, the crRNAs and csRNAs driven by the pol II promoter did not seem to cause any gene disruption compared to the control, indicating that the crRNAs and csRNAs may be non-functional. This is because without the additional direct repeat sequence, the Cpf1 protein cannot process the transcribed crRNAs and csRNAs, leaving the 3' poly-A tail still linked to the crRNA, thus preventing the function of the transcribed crRNAs and csRNAs.

Further, it is noted that catRNAshad significant higher gene disruption efficiency in all the tested three genes either in the case of pol II promoter or in the case of pol III promoter. This was due to the structure of truncated pre-tRNA, which increases the stability of the whole catRNA molecule significantly.

Example 2: Efficient Gene Activation by gRNAs in Combination with dCpf1

While Cpf1 has been utilized for gene disruption, gene regulation with catalytically dead LbCpf1 (dCpf1) is not well studied. dCpf1 comprises a D832A mutation compared to the wild type LbCpf1.

Figure 5:
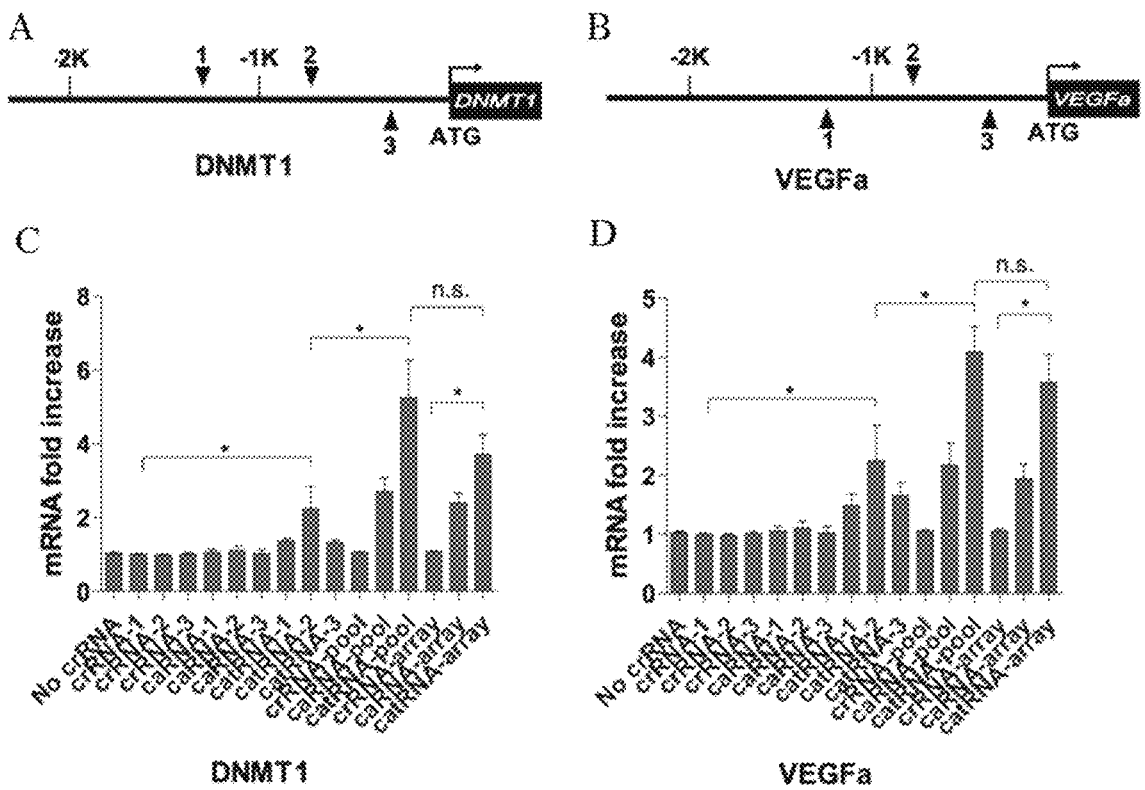
FIG. 5: Synergistic gene activation with the dCpf1-VP64 activator and a pool or an array of guide RNAs. A and B: the position of three target loci in DNMT1 and VEGFa promoters respectively. C and D: expression of DNMT1 and VEGFa genes respectively. Bar, SE. n=3. *, P<0.05, , P<0.01, *, P<0.001, ****, P<0.0001 determined by the Mann-Whitney test.

To implement dCpf1 in gene activation, we tethered four copies of the herpes simplex virus-derived VP16 (VP64) activator domain with dCpf1 to make the dCpf1-VP64 fusion protein. To test whether endogenous genes could be activated with this construct, we co-transfected into 293T cells a plasmid harboring this sequence alone (control) or in combination with plasmids encoding crRNA, caRNA or catRNA targeting different positions in the promoter region of the DNMT1 and VEGFa promoters respectively. The arrows in FIGS. 5A and 5B indicate the specific target loci in the promoter region of each gene. Gene expression was measured by quantitative real-time PCR 48 hours post-transfection. A slight gene up-regulation was detected with caRNAs compared with crRNAs targeting the DNMT1 or VEGFa promoter. Nevertheless, significant gene up-regulation was observed with catRNAs targeting the DNMT1 or VEGFa promoter (FIGS. 5C and 5D).

The crRNAs, caRNAs and catRNAs used in the following examples have the same structure as those used in Example 1, the only difference is the spacer sequence, so only the spacer sequence will be provided in the following examples. The space sequences used in this example are listed in the following Table 2.

TABLE 2

Spacer sequences targeting the promoter region of the DNMT1 and VEGFa genes.

| Name | Spacer Sequences |
|------|------------------|
| DNMT1-1 | TCAGCACCATTTGTTAAAGACAC (SEQ ID NO: 13) |
| DNMT1-2 | CGCGCGAAAAGCCGGGGCGCCTG (SEQ ID NO: 14) |
| DNMT1-3 | TGAGAGCCCTTGAGTAAAGTCCT (SEQ ID NO: 15) |

TABLE 2-continued

Spacer sequences targeting the promoter
region of the DNMT1 and VEGFa genes.

| Name | Spacer Sequences |
|---|---|
| VEGFa-1 | TGACCTCCCAAACAGCTACATAT (SEQ ID NO: 16) |
| VEGFa-2 | CTGCTCCCTCCTCGCCAATGCCC (SEQ ID NO: 17) |
| VEGFa-3 | TCCCCAAATCACTGTGGATTTTG (SEQ ID NO: 18) |

This result in FIGS. 5C and 5D showed that dCpf1 can efficiently work with crRNA, caRNA or catRNA for gene activation, while caRNA and catRNA exhibited a relative higher efficiency compared with crRNA. The catRNA targeting the second position of the promoter region in both DNM1 gene and VEGF gene achieved the highest activation.

Example 3: Synergistic Activation by Pooled or Arrayed gRNAs

Figure 4:
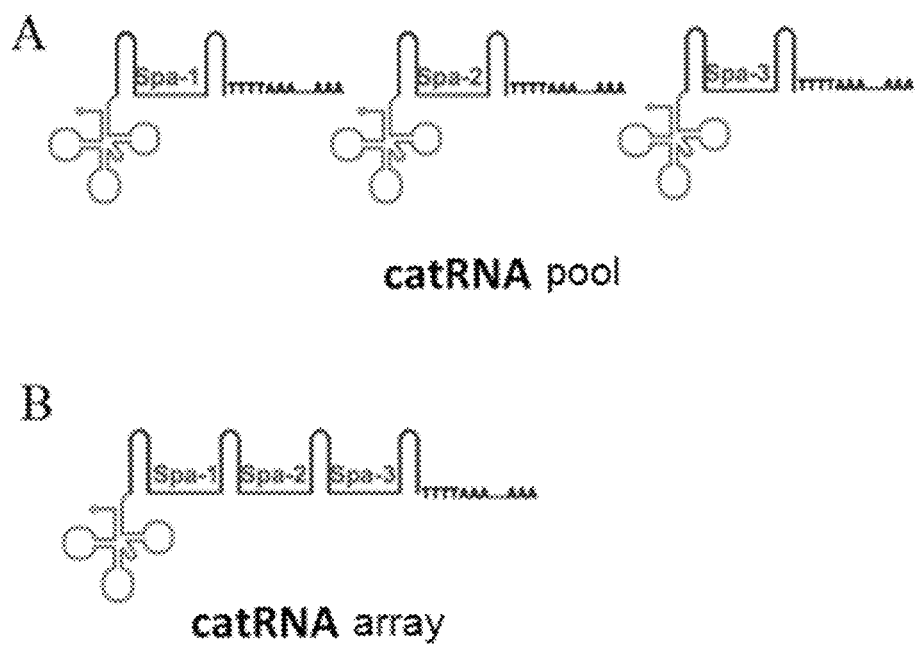
FIG. 4: Schematic representation of a catRNA pool or an catRNA array for synergistic gene activation. Spa: Spacer.

To test whether a synergistic effect on gene activation exists using different gRNAs simultaneously targeting a promoter, we co-transfected into 293T cells the dCpf1-VP64 fusion protein with pooled or arrayed crRNAs, caRNAs, catRNAs respectively targeting the same loci in Example 2. FIG. 4 is a schematic representation of the catRNA pool and catRNA array used in this experiment. The spacer sequences are the same as those used in Example 2.

The results targeting the DNMT1 promoter were shown in FIG. 5C. No significant gene activation was observed with the pooled crRNAs or arrayed crRNA compared with a single crRNA. However, significant gene activation was detected with pooled caRNAs or arrayed caRNAs, which reach a level similar to those achieved by a single catRNA. Such gene activation was further improved with pooled catRNAs and arrayed catRNAs, with pooled catRNAs reached the highest gene activations of 5.3-fold. It was noted that catRNAs always presented a better performance than caRNA either in the form of a pool or an array. Similar trends were observed in the case of VEGFa promoter, as shown in FIG. 5D.

The above results showed that while a single caRNA and catRNA can induce gene activation efficiently, the pooled and arrayed caRNAs or catRNAs exhibited a synergistic effect on the gene activation.

Example 4: Gene Activation Enhanced by Multiple Strong Activators

Because Pol-II crRNAs were not functional and Pol-II caRNAs and Pol-II catRNAs were always more efficient than Pol-III caRNAs and Pol-III catRNAs, we used Pol-III crRNAs, Pol-II caRNAs, and Pol-II catRNAs in future experiments.

To extend the utility of dCpf1 activators, we tethered dCpf1 to a VP64 activator or a strong synthetic VPR activator, which comprises the VP64 activator, the human NF-KB p65 activation domain, and the Epstein-Barr virus-derived R transactivator (Rta) (Chavez A et al., 2015), and co-transfected it alone (control) or in combination with a single crRNA, caRNA or catRNA targeting the same locus in the promoter region of DNMT1 or VEGFa gene into 293T cells. Gene expression was calculated by quantitative real-time PCR 48 hours post-transfection.

The same gRNAs targeting the second position of the DNMT1 promoter and the first position of the VEGFa as in Example 3 were used.

Figure 6:
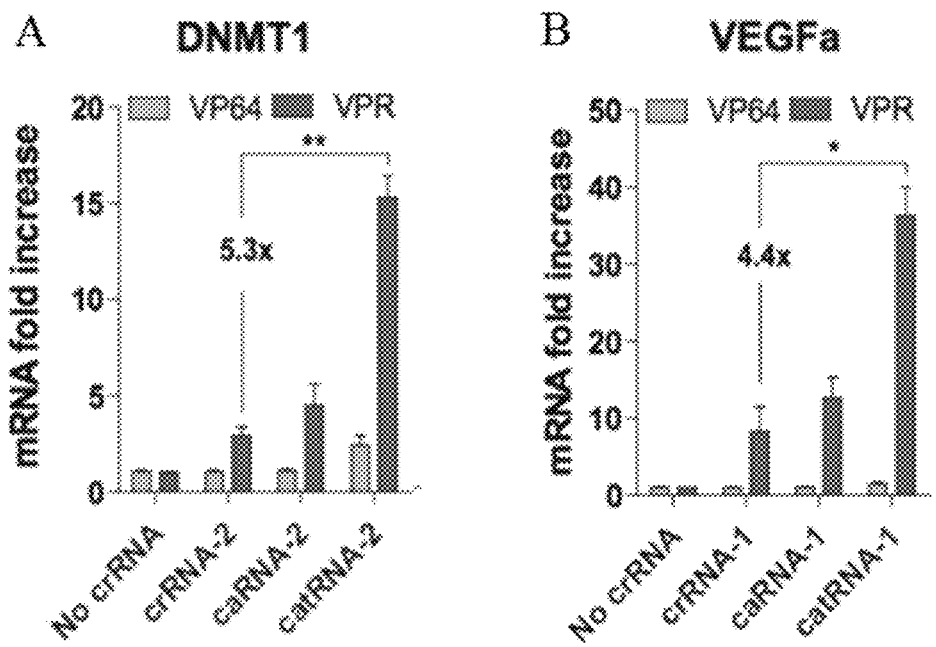
FIG. 6: Efficient gene activation with the dCpf1-VPR activator and a single guide RNA targeting the DNMT1 promoter (A) or the VEGFa promoter (B). Bar, SE. n=3. *, P<0.05, , P<0.01, *, P<0.001, ****, P<0.0001 determined by the Mann-Whitney test.

As shown in FIG. 6, dCpf1-VPR led to robust transcriptional up-regulation from both of the target gene promoters. Consistent with previous observations with dCas9 activators, gene activation by the dCpf1 activator was more efficient when multiple strong activator domains were recruited to the targeted promoter. Fusion of dCpf1-VPR showed superior activity relative to that of dCpf1-VP64. In the robust activation mediated by VPR, caRNA presented a mild increased gene activation compared with crRNA in both DNMT1 and VEGFa gene promoters, while the DNMT1 and VEGFa activation induced by catRNAs was about 5.3-fold and 4.4-fold higher than that induced by crRNAs, further supporting the advantage of using caRNAs and catRNAs, in particularly catRNAs for gene perturbation.

This result indicated that the inclusion of multiple activators was able to facilitate the gene activation efficiency compared to the case in which only one activator was used.

Example 5: Simultaneous Activation by Pooled or Arrayed gRNAs

Figure 7:
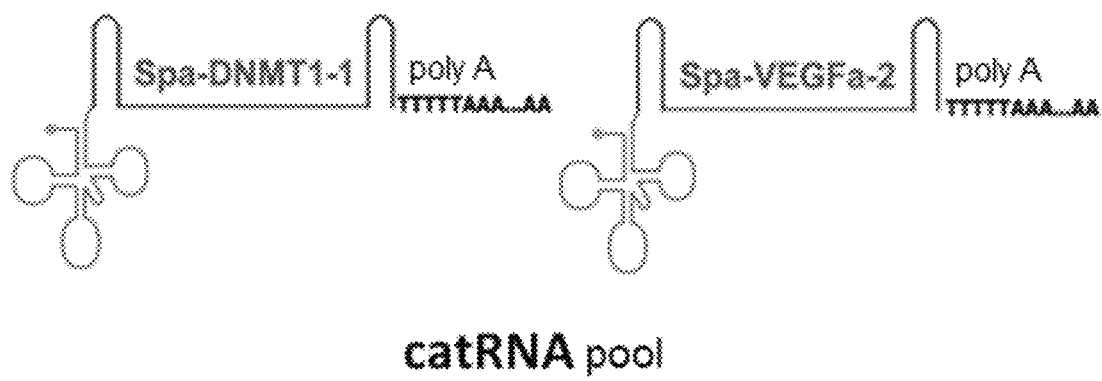
FIG. 7: Schematic representation of a catRNA pool or an catRNA array for simultaneous gene activation. Spa: Spacer.
Figure 7:
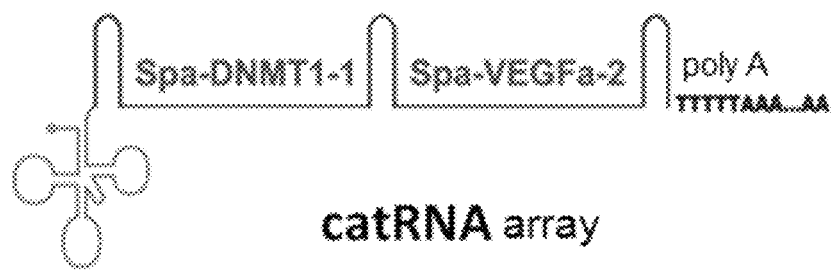

The capability of processing multiple crRNAs within a single transcript makes Cpf1 a good platform for multiple gene regulation. To test whether a simultaneous gene activation can be achieved using different caRNAs and catRNAs, we co-transfected into 293T cells the dCpf1-VPR fusion protein with pooled or arrayed gRNAs targeting both the DNMT1 and VEGFa promoter. Gene expression was measured by quantitative real-time PCR 48 hours post-transfection. FIG. 7 is a schematic representation of the catRNA pool andcatRNA array-used in this experiment.

The spacer sequences used in the gRNAs of this example are DNMT1-1 and VEGFa-2, which are the same as those used in Example 3.

Figure 8:
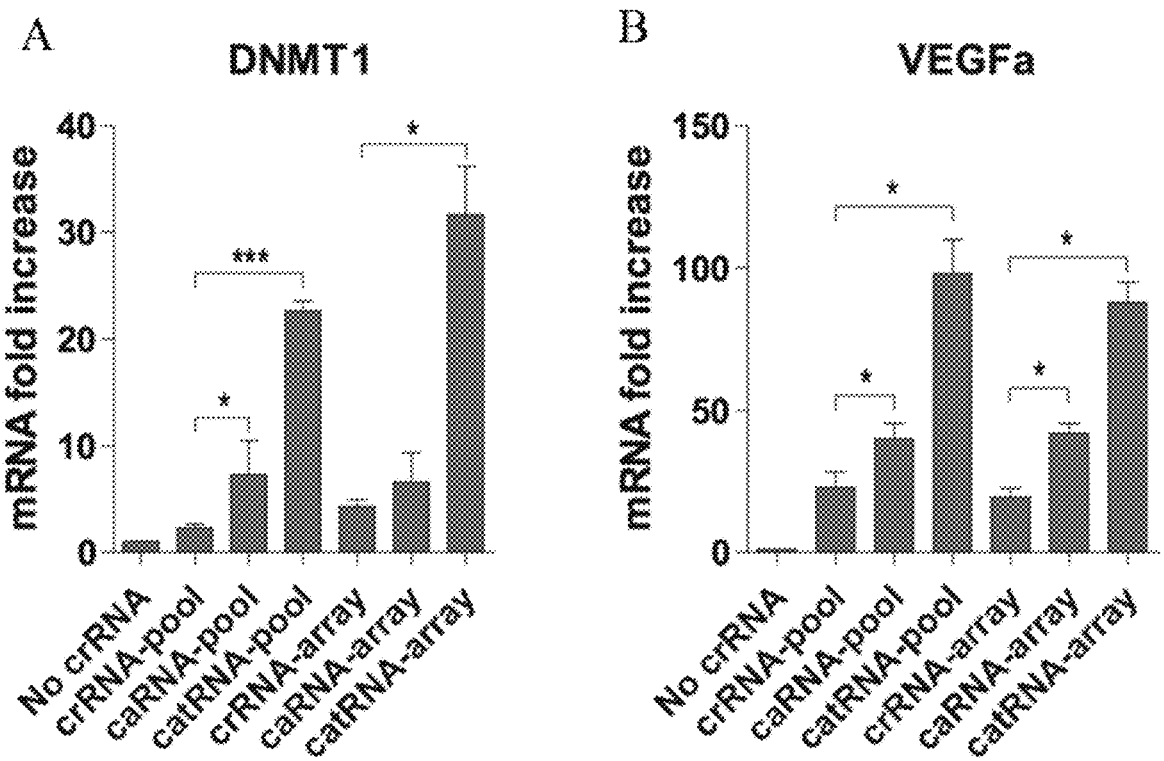
FIG. 8: Simultaneous DNMT1 and VEGFa gene activation with the dCpf1-VPR activator and a pool or an array of guide RNAs. A. Gene activation in DNMT1 gene; B. Gene activation in VEGFa gene. Bar, SE. n=3. *, P<0.05, , P<0.01, *, P<0.001, ****, P<0.0001 determined by the Mann-Whitney test.

The results are shown in FIG. 8. It is clear that simultaneous activation in both GNMT1 and VEGFa was achieved with either pooled or arrayed caRNAs or catRNAs. Specifically, pooled and arrayed caRNAs led to significantly increased gene activation compared to crRNAs, while catRNAs further enhanced such increase.

The above results indicated that the caRNAs and catRNAs can be used for simultaneous activation of multiple target genes efficiently.

Example 6: Gene Disruption Using catRNA with Different Length of Spacers

Truncated guide RNA has been reported to increase the gene-targeting specificity. To test whether gene disruption can be achieved using catRNAs with truncated spacers, we generated catRNAs targeting DNMT1 or VEGRa gene with different length of spacers and co-transfected it with LbCpf1 into 293T cells. Cells were harvested for genomic DNA extraction 72 hours after DNA transfection. Specific knockouts in DNMT1 and VEGFa genes were measured with TIDE online software.

The spacer sequences in the catRNAs used in this example are listed in the following Table 3.

TABLE 3

Spacer sequences with different lengths.

| Name | Spacer Sequences |
|---|---|
| DNMT1-24 bp | CTGATGGTCCATGTCTGTTACTCG (SEQ ID NO: 19) |
| DNMT1-20 bp | CTGATGGTCCATGTCTGTTA (SEQ ID NO: 20) |
| DNMT1-18 bp | CTGATGGTCCATGTCTGT (SEQ ID NO: 21) |
| DNMT1-17 bp | CTGATGGTCCATGTCTG (SEQ ID NO: 22) |
| DNMT1-16 bp | CTGATGGTCCATGTCT (SEQ ID NO: 23) |
| DNMT1-15 bp | CTGATGGTCCATGTC (SEQ ID NO: 24) |
| DNMT1-14 bp | CTGATGGTCCATGT (SEQ ID NO: 25) |
| VEGFa-24 bp | CTAGGAATATTGAAGGGGGCAGGG (SEQ ID NO: 26) |
| VEGFa-20 bp | CTAGGAATATTGAAGGGGC (SEQ ID NO: 27) |
| VEGFa-18 bp | CTAGGAATATTGAAGGGG (SEQ ID NO: 28) |
| VEGFa-17 bp | CTAGGAATATTGAAGGG (SEQ ID NO: 29) |
| VEGFa-16 bp | CTAGGAATATTGAAGG (SEQ ID NO: 30) |
| VEGFa-15 bp | CTAGGAATATTGAAG (SEQ ID NO: 31) |
| VEGFa-14 bp | CTAGGAATATTGAA (SEQ ID NO: 32) |

Figure 9:
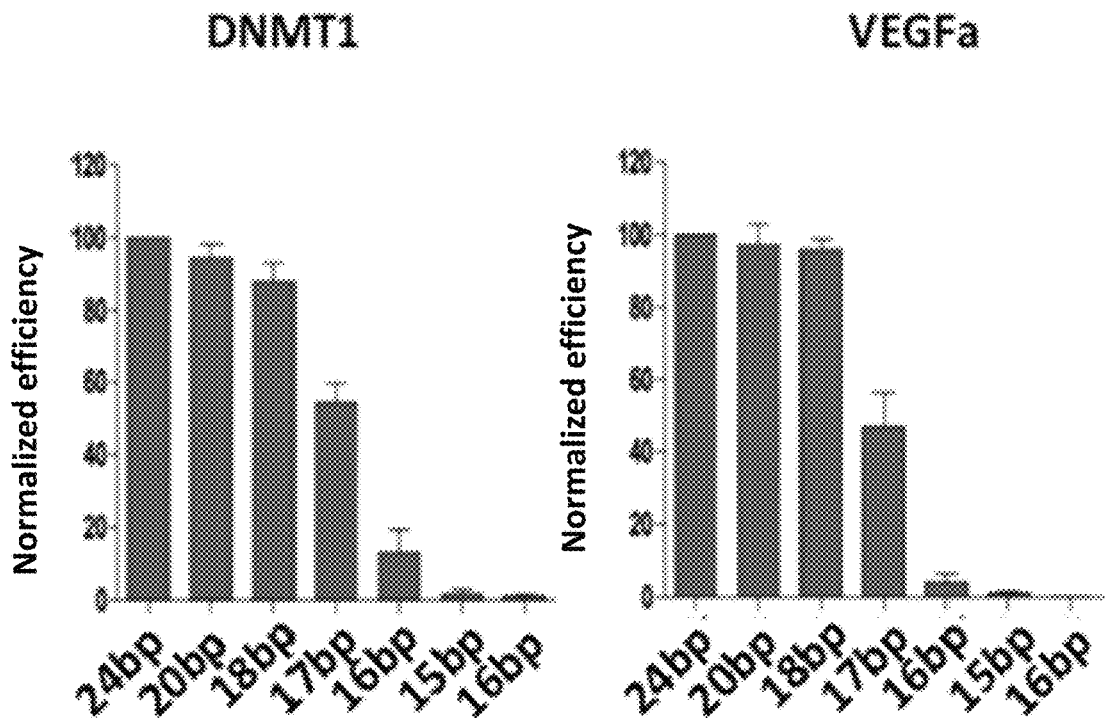
FIG. 9: Targeted gene disruption with catRNAs with different length of spacers. A. Gene disruption in DNMT1 gene; B. Gene disruption in VEGFa gene. Efficiency was normalized relative to the catRNA with a 24-bp spacer. Bar, SE. n=3. *, P<0.05, , P<0.01, *, P<0.001, ****, P<0.0001 determined by the Mann-Whitney test.

Results shown in FIG. 9 revealed that the gene disruption was detectable when the spacer sequence is at least 16 bp in length, while a minimal of 17 bp was required for efficient gene disruption.

Example 7: Generation of Gene Edited CART Cells

To imply the usage of catRNA on immunotherapy, especially chimeric antigen T cell therapy, we generated gene-modified CART cells by targeting TRAC, TRBC, B2m, CD52 GR, dCK and PD-1. CD4 and CD8 T cells mixed at an equal ratio were used as raw material in this experiment.

Transcribed Cpf1 mRNA and chimeric guide RNA were electroporated in vitro into the T cells according to the following protocol. Briefly, T cells were first stimulated by anti-CD3/CD28 beads at a bead to cell ratio of 3:1, and 1 day later CAR transgene was introduced by lentivial transduction. Then, 2 to 4 days later after stimulation, T cells were washed with Opti-MEM two times and then resuspended in Opti-MEM at a final concentration of $1\times10^7$ cells/ml. Subsequently, 20 µg of LbCpf1 mRNA were electroporated into the cells with 20 µg of chimeric guide RNA together in a single electroporation, or before the electrotroporation of the latter in a separate electroporation, in a 2-mm cuvette using a BTX830 electroporator (Harvard Apparatus BTX) at 400 V for 700 µs. Following electroporation, the cells were immediately placed in 2 ml of pre-warmed antibiotic-free culture medium and incubated at 37° C. and 5% $CO_2$. Cells were harvested for genomic DNA extraction 72 hours after electroporation, and gene disruption efficiency was calculated by TIDE online software.

Spacer sequences used in the catRNAs in this example are listed in the following Table 4.

TABLE 4

Spacer sequences used for the preparation of CART cells.

| Name | Spacer Sequence |
|---|---|
| TCRα-1 | ATTCTCAAACAAATGTGTCACAA (SEQ ID NO: 33) |
| TCRα-2 | CATGTGCAAACGCCTTCAACAAC (SEQ ID NO: 34) |
| TCRα-3 | CACATGCAAAGTCAGATTTGTTG (SEQ ID NO: 35) |
| TCRα-4 | TTGCTCCAGGCCACAGCACTGTT (SEQ ID NO: 36) |
| TCRα-5 | TCTGTGATATACACATCAGAATC (SEQ ID NO: 37) |
| TCRα-6 | TGACACATTTGTTTGAGAATCAA (SEQ ID NO: 38) |
| TCRα-7 | TTTGAGAATCAAAATCGGTGAAT (SEQ ID NO: 39) |
| TCRα-8 | AGAATCAAAATCGGTGAATAGGC (SEQ ID NO: 40) |
| TCRα-9 | GAGTCTCTCAGCTGGTACACGGC (SEQ ID NO: 41) |
| TCRβ-1 | AGCCATCAGAAGCAGAGATCTCC (SEQ ID NO: 42) |
| TCRβ-2 | CCTCGGTGTCCTACCAGCAAGGG (SEQ ID NO: 43) |
| TCRβ-3 | GCCCTATCCTGGGTCCACTCGTCA (SEQ ID NO: 44) |
| TCRβ-4 | GGTGTGGGAGATCTCTGCTTCTGA (SEQ ID NO: 45) |
| CD52-1 | TATCTGTACCATAACCAGGAGGC (SEQ ID NO: 46) |
| CD52-2 | TCCTGAGAGTCCAGTTTGTATCT (SEQ ID NO: 47) |
| CD52-3 | GCTGGTGTCGTTTTGTCCTGAGA (SEQ ID NO: 48) |
| CD52-4 | CTTTTCTTCGTGGCCAATGCCAT (SEQ ID NO: 49) |
| CD52-5 | TTCGTGGCCAATGCCATAATCCA (SEQ ID NO: 50) |
| B2m-1 | ATCCATCCGACATTGAAGTTGAC (SEQ ID NO: 51) |
| B2m-2 | GCTGTGCTCGCGCTACTCTCTCT (SEQ ID NO: 52) |
| PD-1 | ACCTTCCGCTCACCTCCGCCTGAG (SEQ ID NO: 53) |
| PD-2 | TGCCCTTCCAGAGAGAAGGGCAG (SEQ ID NO: 54) |
| PD-3 | TCTGCAGGGACAATAGGAGCCAG (SEQ ID NO: 55) |
| PD-4 | TCCTCAAAGAAGGAGGACCCCTC (SEQ ID NO: 56) |
| PD-5 | CAGTGGCGAGAGAAGACCCCGGA (SEQ ID NO: 57) |
| PD-6 | CTAGCGGAATGGGCACCTCATCC (SEQ ID NO: 58) |
| PD-7 | CTCAGGAGAAGCAGGCAGGGTGC (SEQ ID NO: 59) |
| PD-8 | CAACACATCGGAGAGCTTCGTGC (SEQ ID NO: 60) |
| PD-9 | ATCTGCGCCTTGGGGGCCAGGGA (SEQ ID NO: 61) |

Figure 11:
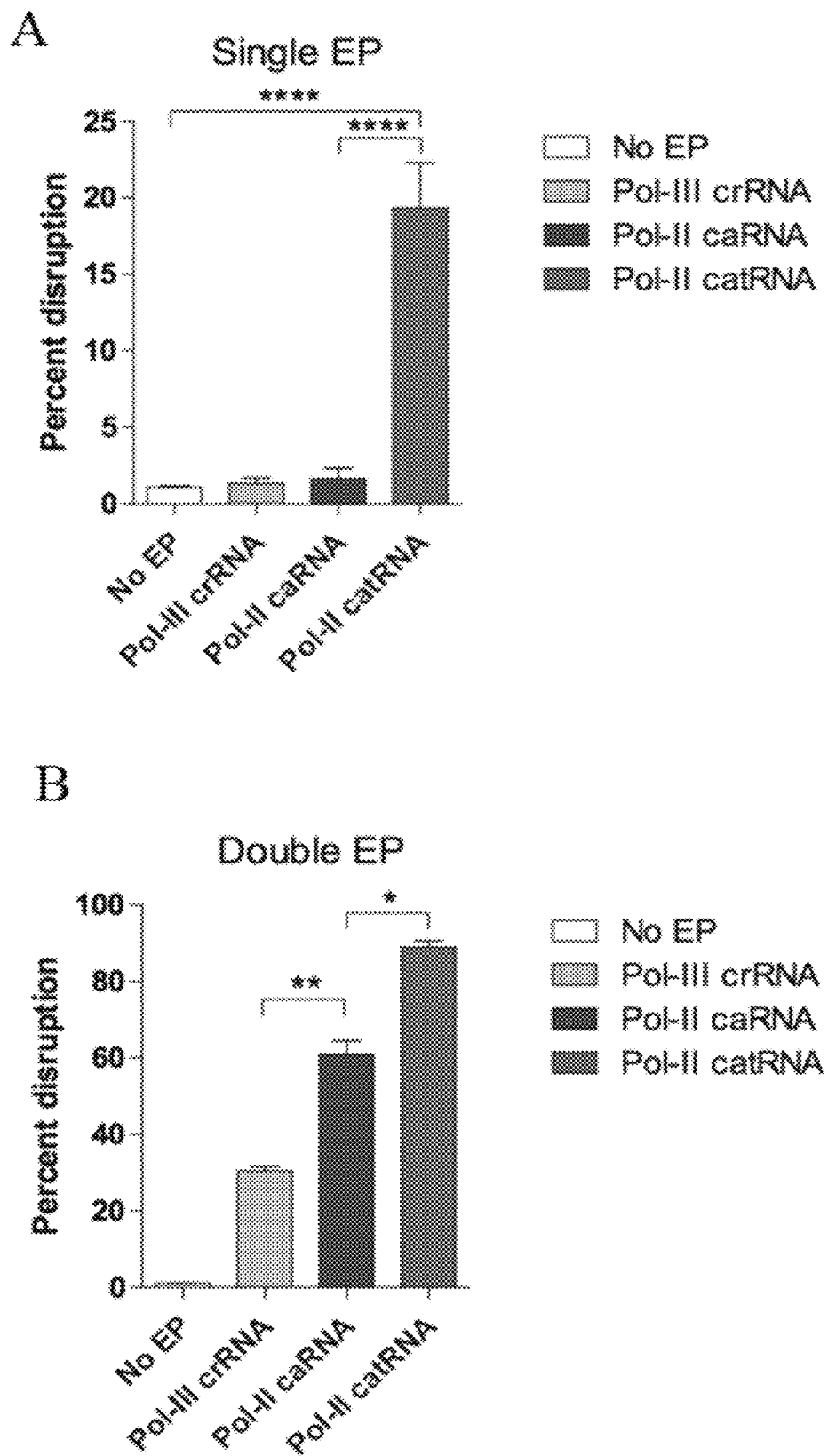
FIG. 11: Disruption of TRAC with guide RNAs using electroporation. A. Disruption efficiency resulted from a single electroporation (i.e., Cpf1 mRNA and guide RNAs were electroporated at the same time); B. Disruption efficiency resulted from a double electroporation (i.e., Cpf1 mRNA was electroporated followed by the electroporation of guide RNAs). Bar, SE. n=3. *, P<0.05, , P<0.01, *, P<0.001, ****, P<0.0001 determined by the Mann-Whitney test.

FIG. 11B shows that catRNA results 3-folds gene disruption efficiency of crRNA and 1.5-folds of caRNA with sequential electro-delivery mode. When single electroporation of Cpf1 mRNA and catRNA was used, around 20% gene disruption can be achieved, however, no detectable gene disruption were achieved with either crRNA or caRNA (FIG. 11A).

Substantial surface CAR transgene expression and endogenous gene ablation was confirmed by flow-cytometry. $5\times10^6$ CD4+CD8 T cells were transfected with 20 µg in vitro transcribed LbCpf1 mRNA alone or in combination with 10 µg chimeric guide catRNAs directed for different target gene or combinations thereof. Corresponding antibodies specific for the target gene or combinations thereof were used 3 days post transfection for readout of flow cytometry analysis. The same CD4+CD8 T cells transfected with LbCpf1 mRNA alone (i.e., without catRNA) was used as a control in this experiment. The results are shown in FIGS. 12-17.

Figure 12:
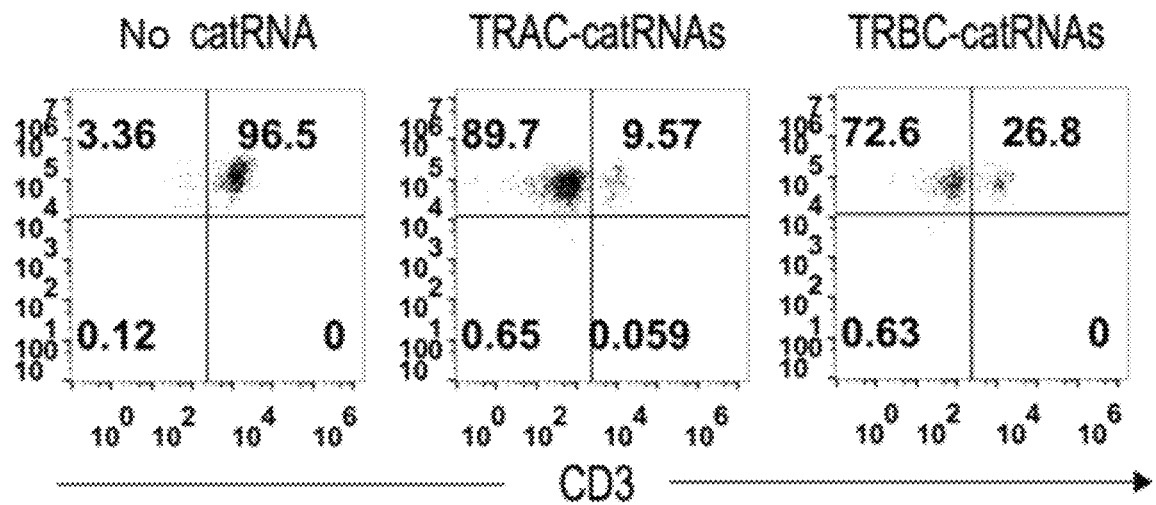
FIG. 12: Flow cytometry analysis of the activity of Cpf1 with catRNA specific for TRAC or TRBC in T cells.

FIG. 12 showed the flow cytomytry results of catRNAs targeting TRAC or TRBC, CD3 antibody was used for the detection of TCR/CD3 complex expressed on CART cells. When no catRNA was used, the number of positive cells detected with the TCR/CD3 marker is around 96.5%, which significantly decreased to 9.57% in the case of TRAC-catRNAs and 26.8% in the case of TRBC-catRNAs. This result confirmed the successful disruption of TRAC or TRAB using catRNAs in the CD4+CD8 cells. The negative cells which do not express TRAC or TRBC were useful CART cells.

Figure 13:
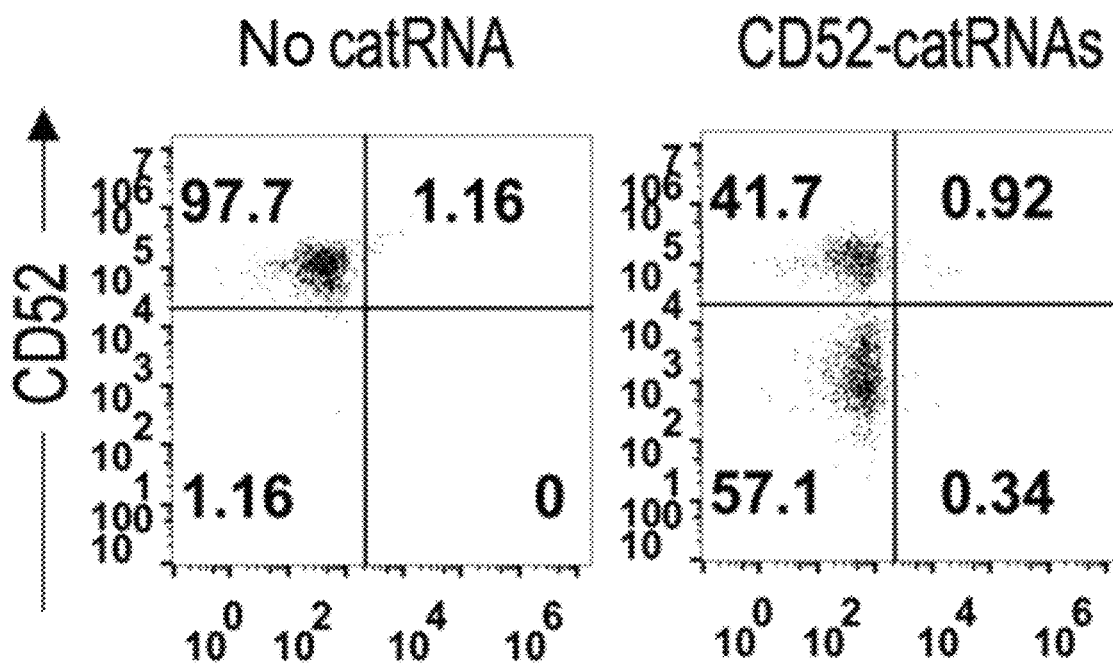
FIG. 13: Flow cytometry analysis of the activity of Cpf1 with catRNA specific for CD52 in T cells.

FIG. 13 showed the flow cytometry results of catRNAs targeting CD52. When no catRNA was used, the number of positive cells detected with the CD52 marker is around 97.7%, which significantly decreased to 41.7% in the case of CD52-catRNA was used. This result confirmed the successful disruption of CD52 using catRNA in the CD4+CD8 cells. The negative cells that do not express CD52 were useful CART cells.

Figure 14:
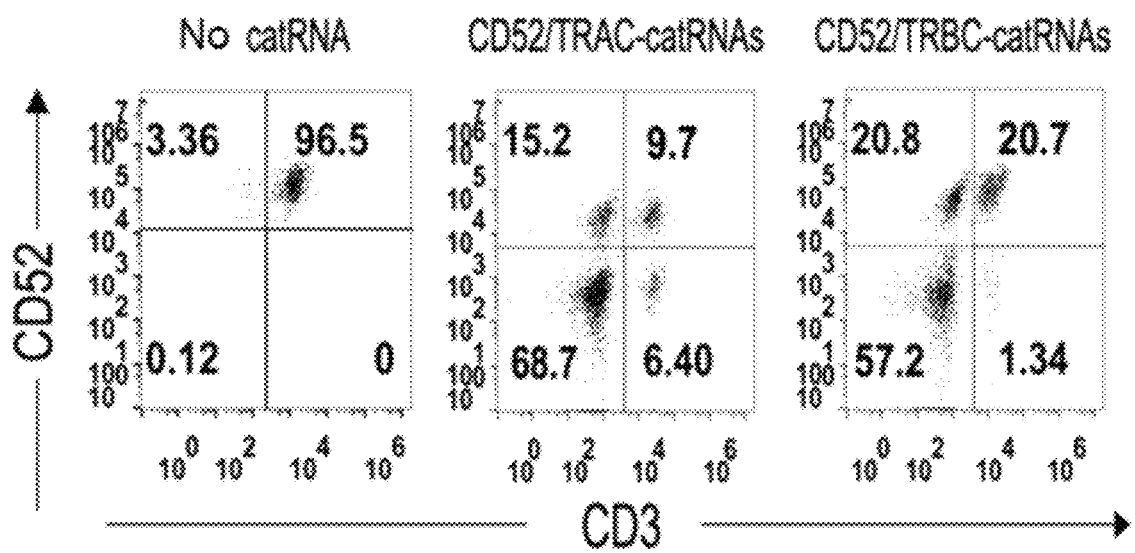
FIG. 14: Flow cytometry analysis of the activity of Cpf1 with catRNA specific for TRAC/CD52 or TRBC/CD52 in T cells.

FIG. 14 showed the flow cytometry results of catRNAs targeting both TCR and CD52, CD3 antibody was used for the detection of TCR/CD3 complex expressed on CART cells. When no catRNA was used, the number of positive cells detected with the CD3/CD52 marker is around 98.2%. The TCR/CD52 double deficient cell population reached to 68.7% in the case of TRAC and CD52 catRNAs were used, and increased to 57.2% in the case of TRBC and CD52 catRNAs ware used. This result confirmed the successful disruption of both TCR and CD52 using catRNAs in the CD4+CD8 cells. The double negative cells that do not express TCR and CD52 were useful CART cells.

Figure 15:
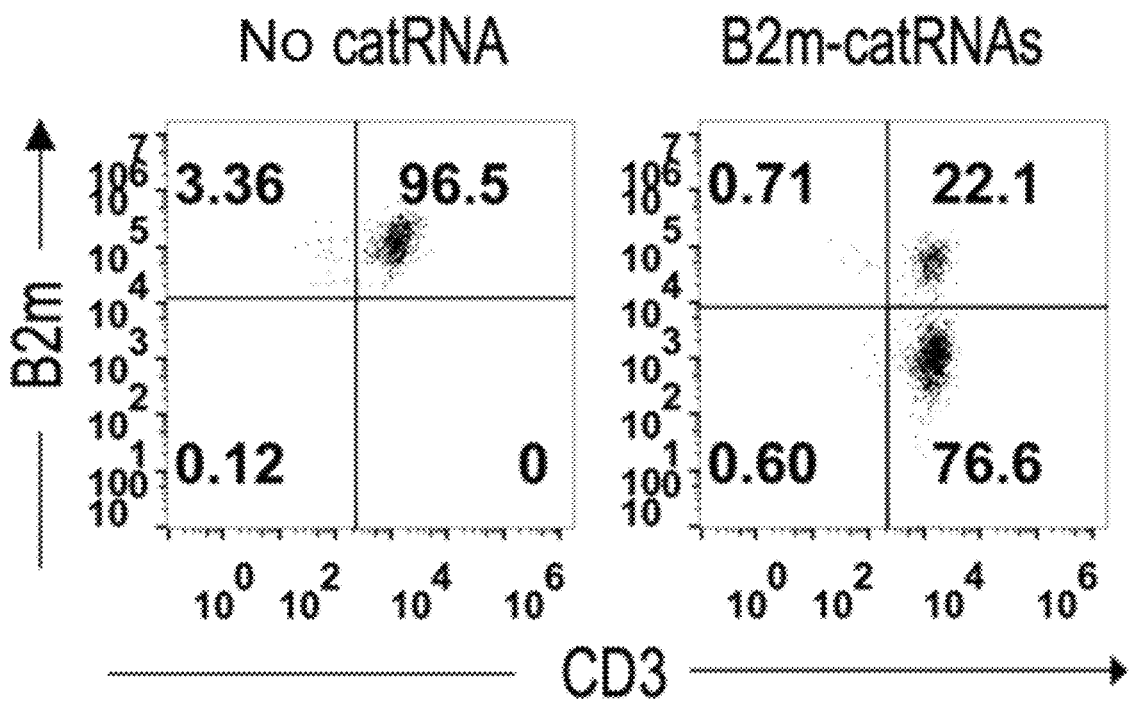
FIG. 15: Flow cytometry analysis of the activity of Cpf1 with catRNA specific for B2m in T cells.

FIG. 15 showed the flow cytometry results of catRNAs targeting B2M. When no catRNA was used, the number of positive cells detected with the B2M marker is around 96.5%, which significantly decreased to 22.1% in the case of B2M-catRNA was used. This result confirmed the successful disruption of B2M using catRNA in the CD4+CD8 cells. The negative cells that do not express B2M were useful CART cells.

Figure 16:
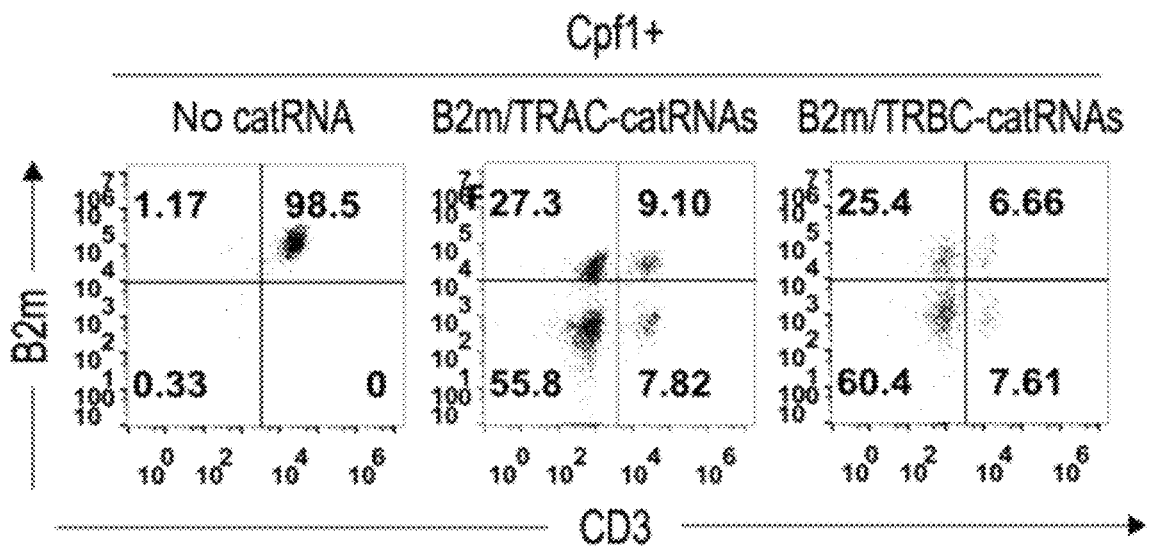
FIG. 16: Flow cytometry analysis of the activity of Cpf1 with catRNA specific for TRAC/B2m or TRBC/B2m in T cells.

FIG. 16 showed the flow cytometry results of catRNAs targeting both TCR and B2M, CD3 antibody was used for TCR/CD3 complex expression on CART cells. When no catRNA was used, the number of positive cells detected with the CD3/B2M marker is around 98.5%. The TCR/B2M double deficient cell population reached to 55.8% in the case of TRAC and B2McatRNAs were used, and increased to 60.4% in the case of TRBC and B2McatRNAs ware used. This result confirmed the successful disruption of both TCR and B2M using catRNAs in the CD4+CD8 cells. The double negative cells that do not express TCR and B2M were useful CART cells.

Figure 17:
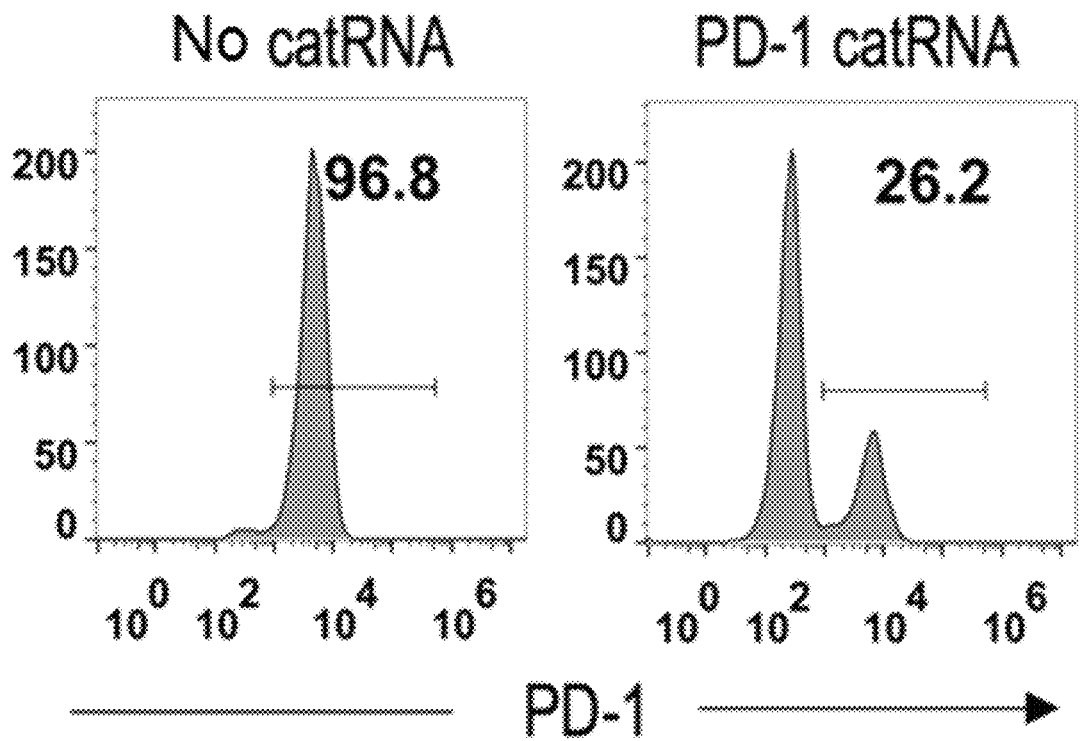
FIG. 17: Flow cytometry analysis of the activity of Cpf1 with catRNA specific for PD-1 in T cells.

FIG. 17 showed the flow cytometry results of catRNAs targeting PD-1. When no catRNA was used, the number of positive cells detected with the PD-1 marker is around 96.8%, which significantly decreased to 26.1% in the case of PD-1-catRNA was used. This result confirmed the successful disruption of PD-1 using catRNA in the CD4+CD8 cells. The negative cells that do not express PD-1 were useful CART cells.

Example 8: Generation of Gene Edited CART Cells

We further generated gene edited CART cells using the method according to the present invention. CD4+CD8 T cells from three healthy human donors were used as raw materials in this experiment.

Transcribed Cpf1 mRNA and chimeric guide crRNA were electroporated in vitro into the T cells according to the following protocol. Briefly, T cells were first stimulated by anti-CD3/CD28 beads at a beads to cell ratio of 3:1, and 1 day later CAR transgene was introduced by lentivial transduction. Then, 2 to 4 days later after stimulation, T cells were washed with Opti-MEM two times and then resuspended in Opti-MEM at a final concentration of $1\times10^7$ cells/ml. Subsequently, the cells (0.1 ml) were mixed with prepared Cpf1-catRNA complex (obtained by pre-incubating 5 µg of LbCpf1 protein with 20 µg of catRNA at room temperature for 10 minutes) and electroporated in a 2-mm cuvette into T cells using a BTX830 electroporator (Harvard Apparatus BTX) at 400 V for 700 µs. Following electroporation, the cells were immediately placed in 2 ml of pre-warmed antibiotic-free culture medium and incubated at 37° ° C. and 5% $CO_2$. Cells were harvested for genomic DNA extraction 72 hours after DNA transfection, and gene disruption efficiency was measured by flow cytometry.

Figure 18:
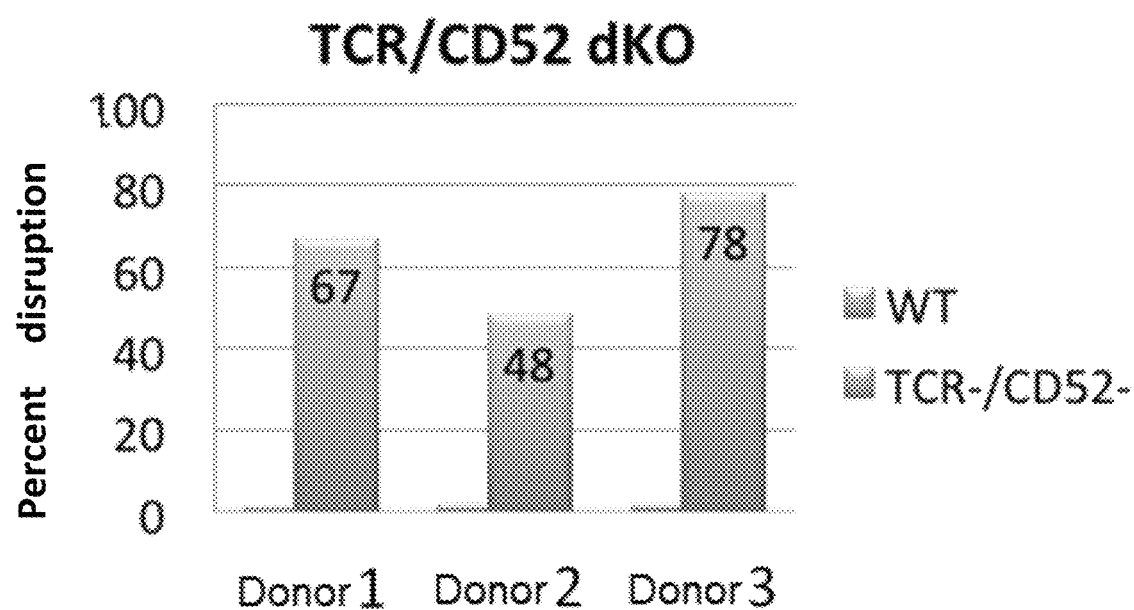
FIG. 18: Targeted gene disruption with catRNA and Cpf1 protein in T cells from different donors.

FIG. 18 showed that TCR/CD52 expression was greatly disputed by electroporation of Cpf1 protein and catRNAs targeting TRAC and CD52 in T cells from all three donors.

REFERENCES

1 Zetsche B, Gootenberg J S, Abudayyeh O O et al. Cpf1 is a single RNA-guided endonuclease of a class 2 CRISPR-Cas system. *Cell* 2015; 163:759-771.
2 Kim D, Kim J, Hur J K, Been K W, Yoon S H, Kim J S. Genome-wide analysis reveals specificities of Cpf1 endonucleases in human cells. *Nat Biotechnol* 2016; 34:863-868.
3 Hur J K, Kim K, Been K W et al. Targeted mutagenesis in mice by electroporation of Cpf1 ribonucleoproteins. *Nat Biotechnol* 2016; 34:807-808.
4 Endo A, Masafumi M, Kaya H, Toki S. Efficient targeted mutagenesis of rice and tobacco genomes using Cpf1 from *Francisella novicida*. *Sci Rep* 2016; 6:38169.
5 Hu X, Wang C, Liu Q, Fu Y, Wang K. Targeted mutagenesis in rice using CRISPR-Cpf1 system. *J GenetGenomics* 2017; 44:71-73.
6 Kim H, Kim S T, Ryu J, Kang B C, Kim J S, Kim S G. CRISPR/Cpf1-mediated DNA-free plant genome editing. *Nat Commun* 2017; 8:14406.
7 Tang X, Lowder L G, Zhang T et al. A CRISPR-Cpf1 system for efficient genome editing and transcriptional repression in plants. *Nat Plants* 2017; 3:17018.
8 Xu R, Qin R, Li H et al. Generation of targeted mutant rice using a CRISPR-Cpf1 system. *Plant Biotechnol J* 2017; 15:713-717.
9 Ungerer J, Pakrasi H B. Cpf1 Is A Versatile Tool for CRISPR Genome Editing Across Diverse Species of Cyanobacteria. *Sci Rep* 2016; 6:39681.
10 Jiang Y, Qian F, Yang J et al. CRISPR-Cpf1 assisted genome editing of *Corynebacterium glutamicum*. *Nat Commun* 2017; 8:15179.

11 Fonfara I, Richter H, Bratovic M, Le Rhun A, Charpentier E. The CRISPR-associated DNA-cleaving enzyme Cpf1 also processes precursor CRISPR RNA. *Nature* 2016; 532:517-521.
12 Zetsche B, Heidenreich M, Mohanraju P et al. Multiplex gene editing by CRISPR-Cpf1 using a single crRNA array. *Nat Biotechnol* 2017; 35:31-34.
13 Wang M, Mao Y, Lu Y, Tao X, Zhu J K. Multiplex Gene Editing in Rice Using the CRISPR-Cpf1 System. *Mol Plant* 2017; 10:1011-1013.
14 Kleinstiver B P, Tsai S Q, Prew M S et al. Genome-wide specificities of CRISPR-Cas Cpf1 nucleases in human cells. *Nat Biotechnol* 2016; 34:869-874.
15 Cong L, Ran F A, Cox D et al. Multiplex genome engineering using CRISPR/Cas systems. *Science* 2013; 339:819-823.
16 Jinek M, Chylinski K, Fonfara I, Hauer M, Doudna J A, Charpentier E. A programmable dual-RNA-guided DNA endonuclease in adaptive bacterial immunity. *Science* 2012; 337:816-821.
17 Mali P, Yang L, Esvelt K M et al. RNA-guided human genome engineering via Cas9. *Science* 2013; 339:823-826.
18 Vakiloroayaei A, Shah N S, Oeffinger M, Bayfield M A. The RNA chaperone La promotes pre-tRNA maturation via indiscriminate binding of both native and misfolded targets. *Nucleic Acids Res* 2017.
19 Ohira T, Suzuki T. Precursors of tRNAs are stabilized by methylguanosine cap structures. *Nat Chem Biol* 2016; 12:648-655.
20 Tang X, Lowder L G, Zhang T et al. A CRISPR-Cpf1 system for efficient genome editing and transcriptional repression in plants. *Nat Plants* 2017; 3:17103.
21 Kim S K, Kim H, Ahn W C et al. Efficient Transcriptional Gene Repression by Type V-A CRISPR-Cpf1 from Eubacterium eligens. *ACS Synth Biol* 2017; 6:1273-1282.
22 Zhang X, Wang J, Cheng Q, Zheng X, Zhao G, Wang J. Multiplex gene regulation by CRISPR-ddCpf1. *Cell Discov* 2017; 3:17018.
23 Brillante N, Gossringer M, Lindenhofer D, Toth U, Rossmanith W, Hartmann R K. Substrate recognition and cleavage-site selection by a single-subunit protein-only RNase P. *Nucleic Acids Res* 2016; 44:2323-2336.
24 Werner M, Rosa E, Nordstrom J L, Goldberg A R, George S T. Short oligonucleotides as external guide sequences for site-specific cleavage of RNA molecules with human RNase P. *RNA* 1998; 4:847-855.
25 Kunzmann A, Brennicke A, Marchfelder A. 5' end maturation and RNA editing have to precede tRNA 3' processing in plant mitochondria. *Proc Natl Acad Sci USA* 1998; 95:108-113.
26 Zhong G, Wang H, Li Y, Tran M H, Farzan M. Cpf1 proteins excise CRISPR RNAs from mRNA transcripts in eukayotic cells. *Nat Chem Biol* 2017.
27 Xie K, Minkenberg B, Yang Y. Boosting CRISPR/Cas9 multiplex editing capability with the endogenous tRNA-processing system. *Proc Natl Acad Sci USA* 2015; 112:3570-3575.
28 Port F, Bullock S L. Augmenting CRISPR applications in Drosophila with tRNA-flanked sgRNAs. *Nat Methods* 2016; 13:852-854.
29 Chavez A, Scheiman J, Vora S et al. Highly efficient Cas9-mediated transcriptional programming. *Nat Methods* 2015; 12:326-328.
30 Qin W, Dion S L, Kutny P M et al. Efficient CRISPR/Cas9-Mediated Genome Editing in Mice by Zygote Electroporation of Nuclease. *Genetics* 2015; 200:423-430.
31 Ren J, Liu X, Fang C, Jiang S, June C H, Zhao Y. Multiplex Genome Editing to Generate Universal CAR T Cells Resistant to PD1 Inhibition. *Clin Cancer Res* 2017; 23:2255-2266.
32 Schumann K, Lin S, Boyer E et al. Generation of knock-in primary human T cells using Cas9 ribonucleoproteins. *Proc Natl Acad Sci USA* 2015; 112:10437-10442.
33 Araujo P R, Yoon K, Ko D et al. Before It Gets Started: Regulating Translation at the 5' UTR. *Comp Funct Genomics* 2012; 2012:475731.
34 Wang L, Wessler S R. Role of mRNA secondary structure in translational repression of the maize transcriptional activator Lc(1,2). *Plant Physiol* 2001; 125:1380-1387.
35 Babendure J R, Babendure J L, Ding J H, Tsien R Y. Control of eukayotic translation by mRNA structure near caps. *RNA* 2006; 12:851-861.
36 Tak Y E, Kleinstiver B P, Nunez J K et al. Inducible and multiplex gene regulation using CRISPR-Cpf1-based transcription factors. *Nat Methods* 2017.

The invention claimed is:

1. An engineered chimeric guide RNA comprising:
   (1) at least one crRNA sequences, and
   (2) at least one additional direct repeat sequences and small RNA species,
   wherein the crRNA sequence is capable of hybridizing with a target locus of interest, and the additional direct repeat sequence and/or small RNA species confers increased stability to the chimeric guide RNA;
   wherein the small RNA species are a truncated form of pre-tRNA.

2. The engineered chimeric guide RNA of claim 1, further comprises one or more elements selected from untranslated region (UTR), poly-A and 5'methylguanosine cap.

3. The engineered chimeric guide RNA of claim 1, wherein the crRNA comprises a spacer sequence, which has a length from 10 to 30 bp.

4. The engineered chimeric guide RNA of claim 1, wherein the engineered chimeric guide RNA is in the form of a pool or an array.

* * * * *